(12) United States Patent
Notomi et al.

(10) Patent No.: US 8,017,357 B2
(45) Date of Patent: *Sep. 13, 2011

(54) METHOD OF AMPLIFYING NUCLEIC ACID BY USING DOUBLE-STRANDED NUCLEIC ACID AS TEMPLATE

(75) Inventors: Tsugunori Notomi, Tochigi (JP); Kentaro Nagamine, Tochigi (JP)

(73) Assignee: Eiken Kagaku Kabushiki Kaisha, Tokyo (JP)

( * ) Notice: Subject to any disclaimer, the term of this patent is extended or adjusted under 35 U.S.C. 154(b) by 1763 days.

This patent is subject to a terminal disclaimer.

(21) Appl. No.: 10/240,460

(22) PCT Filed: Mar. 30, 2001

(86) PCT No.: PCT/JP01/02771
§ 371 (c)(1),
(2), (4) Date: Apr. 8, 2003

(87) PCT Pub. No.: WO01/77317
PCT Pub. Date: Oct. 18, 2001

(65) Prior Publication Data
US 2003/0207292 A1    Nov. 6, 2003

(30) Foreign Application Priority Data
Apr. 7, 2000 (JP) ................................ 2000-111939

(51) Int. Cl.
*C12P 19/34* (2006.01)
*C12Q 1/68* (2006.01)
*C07H 21/04* (2006.01)

(52) U.S. Cl. ..................... 435/91.2; 435/6.12; 536/24.33

(58) Field of Classification Search ............. 435/6, 91.2; 536/24.3, 24.33
See application file for complete search history.

(56) References Cited

U.S. PATENT DOCUMENTS

| 4,683,195 | A |   | 7/1987 | Mullis et al. |
| 4,683,202 | A |   | 7/1987 | Mullis |
| 5,104,791 | A |   | 4/1992 | Abbott et al. |
| 5,270,184 | A |   | 12/1993 | Walker et al. |
| 5,386,022 | A |   | 1/1995 | Sninsky et al. |
| 5,525,462 | A |   | 6/1996 | Takarada et al. |
| 5,595,891 | A |   | 1/1997 | Rose et al. |
| 5,612,199 | A |   | 3/1997 | Western et al. |
| 5,648,211 | A |   | 7/1997 | Fraiser et al. |
| 5,712,124 | A |   | 1/1998 | Walker |
| 5,714,323 | A |   | 2/1998 | Ohshima et al. |
| 5,744,311 | A |   | 4/1998 | Fraiser et al. |
| 5,786,183 | A |   | 7/1998 | Ryder et al. |
| 5,849,547 | A |   | 12/1998 | Cleuziat et al. |
| 5,874,260 | A | * | 2/1999 | Cleuziat et al. .............. 435/91.2 |
| 5,972,618 | A |   | 10/1999 | Bloch et al. |
| 5,981,174 | A |   | 11/1999 | Wolf et al. |
| 6,025,139 | A |   | 2/2000 | Yager et al. |
| 6,033,881 | A |   | 3/2000 | Himmler et al. |
| 6,087,133 | A | * | 7/2000 | Dattagupta et al. .......... 435/91.1 |
| 6,270,962 | B1 |   | 8/2001 | Chamberlin et al. |
| 6,277,607 | B1 |   | 8/2001 | Tyagi et al. |
| 6,410,278 | B1 | * | 6/2002 | Notomi et al. ............... 435/91.2 |
| 6,743,605 | B1 |   | 6/2004 | Rabbani et al. |
| 6,974,670 | B2 | * | 12/2005 | Notomi et al. .................... 435/6 |
| 7,175,985 | B1 | * | 2/2007 | Kanda et al. ...................... 435/6 |
| 7,638,280 | B2 |   | 12/2009 | Kanda et al. |
| 2001/0039334 | A1 |   | 11/2001 | Wright et al. |
| 2003/0104460 | A1 |   | 6/2003 | Rabbani et al. |
| 2003/0165936 | A1 |   | 9/2003 | Rabbani et al. |
| 2003/0165938 | A1 |   | 9/2003 | Rabbani et al. |
| 2003/0165939 | A1 | * | 9/2003 | Rabbani et al. ................... 435/6 |
| 2003/0170681 | A1 |   | 9/2003 | Rabbani et al. |
| 2003/0170682 | A1 |   | 9/2003 | Rabbani et al. |
| 2003/0207292 | A1 |   | 11/2003 | Notomi et al. |
| 2006/0160084 | A1 |   | 7/2006 | Mitani et al. |

FOREIGN PATENT DOCUMENTS

| EP | 0549107 A1 | 6/1993 |
| EP | 0678582 A1 | 10/1995 |
| EP | 0684315 A1 | 11/1995 |
| EP | 0 971 039 A2 | 1/2000 |
| EP | 1020534 A1 | 7/2000 |
| EP | 1231281 A1 | 8/2002 |
| WO | 95/03426 A2 | 2/1995 |
| WO | 96/01327 A1 | 1/1996 |
| WO | WO 97/00330 | 1/1997 |
| WO | 9704131 A1 | 2/1997 |
| WO | 99/66071 A1 | 12/1999 |
| WO | WO 00/28082 | 5/2000 |
| WO | WO 01/34790 A1 | 5/2001 |
| WO | WO 01/34838 A1 | 5/2001 |

OTHER PUBLICATIONS

Walker et al., "Strand Displacement Amplification—An Isothermal, in vitro DNA Amplification Technique," *Nucleic Acid Research*, 20:1691-1696 (1992).

(Continued)

*Primary Examiner* — Young J Kim
*Assistant Examiner* — Angela Bertagna
(74) *Attorney, Agent, or Firm* — LeClairRyan

(57) ABSTRACT

The present invention provides a nucleic acid synthesis method which involves the step of incubating a double-stranded nucleic acid template under conditions that ensure a complementary strand synthesis reaction using a primer as an origin. This method involves the step of placing a region, to which a primer capable of isothermally amplifying the template nucleic acid will anneal, in a condition that ensures base pairing, using an arbitrary primer. The arbitrary primer initiates the complementary strand synthesis reaction, using the double-stranded nucleic acid as a template and DNA polymerases catalyzing the complementary strand synthesis reaction which comprises the destabilization of the double-stranded nucleic acid and strand displacement, thereby providing a region that can undergo base pairing.

5 Claims, 8 Drawing Sheets

OTHER PUBLICATIONS

Notomi et al., "Loop-Mediated Isothermal Amplification of DNA," *Nucleic Acids Research* 28(12):e63(i-vii) (2000).

Notomi et al., "Shinki Idenshi Zofuku hou (LAMP hou) no Genri to Ouyou," *Bio Industry* 18(2):15-23 (2001).

Declaration of Dr. Keith C. Backman (as filed in Control No. U.S. Appl. No. 95/001,146), filed Feb. 11, 2009.

Request for Inter Partes Reexamination of U.S. Patent No. 6,974,670 to Notomi et al. (Control No. U.S. Appl. No. 95/001,146), filed Feb. 11, 2009.

Office Action dated Sep. 24, 2009 for Inter Partes Reexamination of U.S. Patent No. 6,974,670 (Control No. U.S. Appl. No. 95/001,146).

Office Action dated Feb. 16, 2010 for Ex Parte Reexamination of U.S. Patent No. 6,410,278 to Notomi et al. (Control No. U.S. Appl. No. 90/010,702).

Request for Ex Parte Reexamination of U.S. Patent No. 6,410,278 to Notomi et al. (Control No. U.S. Appl. No. 90/010,702), filed Oct. 1, 2009.

Declaration of Keith C. Backman (as filed in Control No. U.S. Appl. No. 90/010,702), filed Oct. 1, 2009.

Tattersall et al., "Rolling Hairpin Model for Replication of Parvovirus and Linear Chromosomal DNA," Nature 263:106-109 (1976).

"DNA Replication" (Second Edition), Arthur Kornberg, Tania A. Baker, W.H. Freeman and Company, 1992, p. 700-703, and p. 713-716.

Third Party observations against EP Application No. 01 917 714.6 (EP 1275715 A1) (Dec. 30, 2010).

Dilger et al., "Lack of Drug Interaction Between Omeprazole, Iansoprazole, Pantoprazole, and Theophylline," J. Clin. Pharmacol. 48:438-444 (1999).

NEB Catalog, p. 121 and 284 (1998).

Lizardi et al., "Mutation Detection and Single-Molecule Counting Using Isothermal Rolling-Circle Amplification," Nat. Gen. 19:225-232 (1998).

Whitcombe et al., "Detection of PCR Products Using Self-Probing Amplicons and Fluorescence," Nat. Biotech. 17:804-807 (1999).

Domingo et al., "High Frequency of Mutations at Position 2144 of the 23S rRNA Gene in Clarithromycin-Resistant *Helicobacter pylori* Strains Isolated in Spain," J. Anti. Chemo. 41:573-574 (1998).

Stratagene Catalog, "Gene Characterization Kits," p. 39 (1988).

\* cited by examiner

METHOD OF AMPLIFYING NUCLEIC ACID BY USING DOUBLE-STRANDED NUCLEIC ACID AS TEMPLATE

TECHNICAL FIELD

The present invention relates to a method for synthesizing a nucleic acid comprising a nucleotide sequence complementary to a template double-stranded nucleic acid.

BACKGROUND ART

The template dependent PCR (Polymerase Chain Reaction) method for synthesizing nucleic acid has been a great driving force for study in the recent bioscience field. The PCR method enables the exponential amplification a nucleic acid comprising a nucleotide sequence complementary to a template nucleic acid using a small amount the template. The PCR method prevails widely at present as a tool for cloning or detecting a gene. In the PCR method, a pair of primers, comprising a complementary nucleotide sequence, is used for both ends of the target nucleotide sequence. The primer pair is designed such that one primer anneals to an extension product provided by another primer. A synthesis reaction proceeds by repeating an annealing to the mutual extension product and a complementary strand synthesis reaction, and an exponential amplification is thus attained.

In the PCR method, a single-stranded nucleic acid template is made by some method and a primer is annealed to the template. Since a template dependent DNA polymerase requires a primer as a replication origin, the preparation of the single-stranded template is considered to be essential, in order to anneal the primer to it in the PCR method. The step of converting a double-stranded template nucleic acid to a single-strand is generally called denaturing. The denaturing is usually carried out by heating. Since other reaction components required for the synthesis of nucleic acid, including DNA polymerase, are heat resistant, the denaturing and successive complementary strand synthesis reactions can be carried out by combining all of the reaction components and further heating the reaction mixture. However, the conventional methods containing the heat treatment step have the problems described below.

First, in the PCR method, the denaturing of double-stranded nucleic acid and the annealing of a primer must be performed in each cycle. For that purpose, a specific mechanism for controlling temperature is required. For example, although a method for monitoring the increase of a reaction product during PCR has been developed, the method cannot be carried out using conventional analytical equipment and, therefore, it is necessary to provide dedicated equipment having a mechanism for controlling temperature to carry out the PCR method as well as a mechanism for monitoring the reaction. Accordingly, if all reactions for the nucleic acid synthesis could be carried out at a constant temperature, the reaction could be monitored easily using conventional analytical equipment. Such a convenient method would simplify not only the equipment but also experimental operation. However, a reaction principle for this method is not currently known.

The reaction specificity of PCR depends on the specificity of primer annealing. A primer can be expected to anneal to a single-stranded nucleic acid with adequate specificity at a high temperature, near a melting temperature. When the temperature is not adequately high, non-specific annealing, and resulting non-specific complementary strand synthesis reactions, often occur. Since the PCR method is accompanied by a complicated temperature change, the reaction mixture may possibly be exposed to a temperature at which a non-specific reaction is apt to occur. This is one of the causes for the non-specific reactions associated with the PCR method.

Several methods for solving the problem of the temperature-dependent non-specific reaction have been proposed. For example, one practically used method uses a DNA polymerase that does not work at a certain temperature or less. Specifically, a temperature sensitive DNA polymerase inhibitor, an antibody against the DNA polymerase, or a variant of DNA polymerase and the like are reportedly used. Further, a method in which the reaction components are put in compartments separated by a partition that is meltable at a high temperature, so that the components are mixed only after heated to an adequate temperature, is also known. At all events, since the PCR method accompanies a complicated temperature change, it is required to use a special component for preventing the non-specific reaction.

Methods of amplifying DNA having a complementary sequence to a target sequence using the target sequence as a template, such as the Strand Displacement Amplification (SDA) method, are also known (Pro.N.A.S., 89, pp. 392-396; 1992, Nucleic Acid, Res., 20, pp. 1691-1696; 1992). In the SDA method, when a complementary strand is synthesized using as a synthesis origin a complementary primer to the 3'-side of a certain nucleotide sequence, a unique DNA polymerase enables synthesis of a complementary strand that displaces the double-strand region at the 5'-side. When reciting "5'-side" or "3'-side" hereinafter, the terms mean the direction of a template strand. This method is called Strand Displacement Amplification because the double-strand portion of the 5'-side is displaced with a complementary strand which has been newly synthesized.

In the SDA method, the step of changing temperature, which is essential for the PCR method, can be omitted by inserting a restriction enzyme recognition sequence in a sequence to which a primer anneals. Namely, a nick provided by the restriction enzyme gives a 3'-OH group that becomes the origin of complementary strand synthesis. The strand displacement and complementary strand synthesis are carried out from the origin and the complementary strand synthesized is dissociated as a single-strand and utilized as the template in the subsequent complementary strand synthesis. Thus, the SDA method does not require a complicated temperature control that has been essential for the PCR method.

Although the temperature control is not necessary in the SDA method, the heat treatment is still necessary to prepare the single-strand needed for primer annealing when double-stranded nucleic acid is used as a template. Further, this method requires both a restriction enzyme that provides a nick and a DNA polymerase with strand displacement activity. Necessity of an additional enzyme leads to an increase in cost. Furthermore, in order to introduce a nick and to not cleave the double-strand (i.e., only one strand is cleaved), a dNTP derivative, such as α-thio dNTP, must be used as a substrate for synthesis so that one of the double-strands has resistance to enzyme digestion. Accordingly, an amplified product obtained by SDA has a configuration different from natural nucleic acid. Thus, restriction enzyme cleavage and use of an amplified product in gene cloning are limited. The use of the dNTP derivative also causes an increase in cost.

As a method for amplifying nucleic acid without a complicated temperature control, Nucleic Acid Sequence-based Amplification (NASBA), which is also called TMA/Transcription Mediated Amplification method, is known. NASBA is a reaction system in which DNA synthesis is carried out using DNA polymerase, a target RNA as a template, and a probe to which T7 promoter has been added. The synthesized DNA is made double-stranded using a second probe, and transcription is performed using T7 RNA polymerase. The double-stranded DNA obtained is used as a template, thereby amplifying a large quantity of RNA (Nature, 350, pp. 91-92, 1991). Transcription using T7 RNA polymerase in NASBA proceeds isothermally. However, NASBA requires RNA as a template, and thus cannot be applied to double-stranded nucleic acid. If the double-stranded nucleic acid is made single-stranded, this reaction can be performed; however, in this case, a complicated temperature control similar to PCR is needed. Further, a combination use of plural enzymes, such as reverse transcription enzyme, RNaseH, DNA polymerase, and T7 RNA polymerase, is essential, which is economically disadvantageous as in SDA. Thus, known nucleic acid amplification reaction methods have the problem of complicated temperature control or the necessity to use plural enzymes.

In order to solve the problem of the temperature control in known nucleic acid synthesis methods, a complementary strand has been synthesized under a specific condition, using a primer as the origin for the synthesis (Published Japanese Translation of International Publication No. Hei 11-509406; WO97/00330). The method recognizes of the fact that the hybridization of nucleic acids having complementary nucleotide sequences occurs in a state of dynamic equilibrium (kinetics). In this prior art method, it is believed that the complementary strand synthesis reaction, using a primer as the origin for the synthesis, may occur at a certain probability, even at a temperature that causes complete denaturing or below. The term "complete denaturing" as used herein means a condition in which most of the double-stranded template nucleic acid becomes single-stranded.

In this report, when a primer and a DNA polymerase with strand displacement activity are combined with the double-stranded template nucleic acid and the temperature is raised, the synthesis of complementary strand was observed at a temperature which did not cause denaturation of a template nucleic acid. However, the reaction efficiency of the complementary strand synthesis without thermal cycling is remarkably lower than that obtained in the PCR method with thermal cycling. In fact, the present inventors performed a supplementary test and confirmed that the reaction had certainly occurred, but the amount of the reaction product obtained by this method did not reach a usable level of a practical nucleic acid synthesis method.

As described above, a nucleic acid synthesis reaction without controlling the temperature and deteriorating the specificity and efficiency of the reaction, has not yet been reported.

DISCLOSURE OF THE INVENTION

An object of the present invention is to provide a nucleic acid synthesis method using double-stranded nucleic acid as a template, wherein the method does not require temperature change and does not result in a deterioration of synthesis efficiency, operability, specificity, or the like. More specifically, it is the object of the present invention to provide a novel nucleic acid synthesis method in which the reaction is carried out by incubating double-stranded nucleic acid as a template together with reaction components, such as a primer and DNA polymerase, at a constant temperature. Another object of the present invention is to provide a method for efficiently amplifying nucleic acid utilizing the synthesis method.

In order to achieve complementary strand synthesis using double-stranded nucleic acid as a template without thermal cycling, the present inventors studied whether the complementary strand synthesis reaction using a primer as the origin for the synthesis could be carried out under a constant temperature condition. The known complementary strand synthesis method, based on the dynamic equilibrium between a double-stranded nucleic acid and a primer (Published Japanese Translation of International Publication No. Hei 11-509406; WO97/00330), does not require the temperature change. However, as previously described, it is difficult to attain practically usable synthesis efficiency using this method. Therefore, the present inventors combined this method with the isothermal nucleic acid synthesis reaction in order to efficiently conduct a complementary strand synthesis based on the dynamic equilibrium without deteriorating specificity. As a result, the inventors discovered that a high level amplification efficiency, which could not be attained by known methods, could be obtained, and completed the present invention. Namely, the present invention relates to the following nucleic acid synthesis method and the nucleic acid amplification method based thereon.

[1] A method for synthesizing nucleic acid using double-stranded nucleic acid as a template, wherein the method comprises:
  a) incubating a double-stranded nucleic acid template and an arbitrary primer in the presence of a DNA polymerase that catalyzes a complementary strand synthesis reaction accompanying strand displacement, under a condition that ensures the synthesis of complementary strand using the arbitrary primer as an origin, such that a region of the target template nucleic acid to be annealed by a primer capable of amplifying the template nucleic acid at a constant temperature is placed in a condition that allows the region to undergo base pairing;
  b) annealing a primer that can amplify the template nucleic acid at a constant temperature, to the region obtained in the step a), which is placed in a condition such that it can undergo base pairing; and
  c) carrying out the complementary strand synthesis using the primer as a synthesis origin.

[2] The method according to [1], wherein the step a) is carried out in the presence of a melting temperature regulator.

[3] The method according to [2], wherein the melting temperature regulator is at least one of compounds selected from the group consisting of betaine, proline, dimethyl sulfoxide, and trimethylamine-N-oxide.

[4] A method for synthesizing a nucleic acid in which a plural number of nucleotides, constituting a specific region of a double-stranded nucleic acid template that is constituted by complementary nucleotide sequences, are connected on a single-strand, wherein the method comprises:
  a) incubating a double-stranded nucleic acid template and an arbitrary primer in the presence of DNA polymerase that catalyzes a complementary strand synthesis reaction accompanying strand displacement under a condition that ensures the synthesis of complementary strand using the arbitrary primer as an origin, such that a region of the target template nucleic acid to be annealed by a second primer, is placed in a condition that allows the region to undergo base pairing;
  b) annealing the second primer to the region obtained in the step a), which is placed in a condition such that it can undergo base pairing, and carrying out the complementary strand synthesis using the second primer as an origin, wherein the 3'-end of the second primer anneals to a region that defines the 3'-side of one of the strands constituting the specific region and the 5'-end of the second primer comprises a nucleotide sequence complementary to an arbitrary region of a complementary strand synthesis reaction product obtained using the primer as an origin;

c) placing a region of the extended product of the second primer synthesized in the step b), to which a first primer will anneal, in a condition such that the region can undergo base pairing, wherein the 3'-end of the first primer anneals to a region that defines the 3'-side of said region in the extended product obtained using the second primer as an origin;

d) annealing the first primer to the region obtained in the step c), which is placed in a condition such that it can undergo base pairing and carrying out the synthesis of complementary strand using the first primer as an origin; and e) allowing self annealing at the 3'-end of the extended product of the first primer synthesized in the step d) to occur and carrying out the synthesis of complementary strand using the extended product itself as a template, and obtaining nucleic acid in which a plural number of the nucleotides constituting the specific region are connected on single strand.

[5] The method according to [4], wherein the arbitrary primer in the step a) is a first primer.

[6] The method according to [4], wherein the step c) is carried out by displacement according to a complementary strand synthesis reaction using as an origin a fourth primer that anneals to the 3'-side of the region of the template annealed by the second primer.

[7] The method according to [4], wherein the step e) further comprises a step of converting the extended product of the first primer into a single strand by displacement according to a complementary strand synthesis reaction using as an origin a third primer that anneals to the 3'-side of the region of the template annealed by the first primer.

[8] The method according to [4], wherein the 5'-end of the first primer comprises a nucleotide sequence complementary to an arbitrary region of the complementary strand synthesis reaction product obtained using the first primer as an origin.

[9] A method for amplifying nucleic acid in which a plural number of nucleotides, constituting a specific region of a double-stranded nucleic acid template that is constituted by complementary nucleotide sequences, are connected on a single-strand, wherein the method comprises:

1) allowing self annealing at the 3'-end of the extended product of the first primer produced by the method according to [7] and carrying out the complementary strand synthesis reaction using the extended product as an origin;

2) annealing the second primer or the first primer to a loop region that is formed by self annealing of the 3'-end and carrying out the synthesis of complementary strand using the primer as an origin;

3) allowing strand displacement of the extended product from the 3'-end to occur by the complementary strand synthesis reaction of the step 2) so that the 3'-end can undergo base pairing;

4) carrying out the complementary strand synthesis reaction using as a template the displaced strand itself obtained in the step 3), which can undergo base pairing and using its 3'-end as an origin to displace a complementary strand synthesized in the step 2) using the loop region as an origin, thereby producing a single-stranded nucleic acid; and 5) repeating the steps 2) to 4) to amplify the desired nucleic acid.

[10] The method according to [9], wherein the method further comprises:

6) carrying out the complementary strand synthesis reaction by self annealing of the 3'-end of the single-stranded nucleic acid produced in the step 4);

7) annealing the second primer or the first primer to a loop region that is formed by self annealing of the 3'-end and carrying out the complementary strand synthesis using the primer as an origin;

8) allowing strand displacement of the extended product from the 3'-end to occur by the complementary strand synthesis reaction of the step 7), so that the 3'-end can undergo base pairing;

9) carrying out the complementary strand synthesis reaction using as a template the displaced strand itself obtained in the step 8), which can undergo base pairing and using its 3'-end as an origin to displace a complementary strand synthesized in the step 7) using the loop region as an origin, thereby producing a single-stranded nucleic acid; and 10) repeating the steps 7) to 9) to amplify the desired nucleic acid.

[11] A method for detecting a target nucleotide sequence in a sample, the method comprising carrying out the amplification method according to [10] and observing whether or not the amplification reaction product has been generated.

[12] A method according to [11], wherein the method according to [10] is carried out in the presence of a nucleic acid detection agent, further comprising determining whether or not the amplification reaction product has been generated based on the signal change of the detection agent.

[13] A method for detecting mutation by the detection method according to [11], wherein mutation in a nucleotide sequence to be amplified prevents the synthesis of complementary strand, at least at one 3'-end that is the origin of the complementary strand synthesis which constitutes the amplification method.

[14] A method for amplifying a nucleic acid in which a plural number of a nucleotides, constituting a specific region of a template double-stranded nucleic acid which is constituted by complementary nucleotide sequences, are connected on a single-strand, wherein the method comprises a step of incubating the following elements:

a target comprising a double-stranded nucleic acid template comprising a specific region to be amplified;

a DNA polymerase that catalyzes the complementary strand synthesis reaction accompanying strand displacement;

a first primer, the 3'-end of which anneals to a region that defines the 3'-side of one of the strands constituting the specific region and the 5'-end of which comprises a nucleotide sequence complementary to an arbitrary region of a complementary strand synthesis reaction product obtained using the primer as a synthesis origin;

a second primer, the 3'-end of which anneals to a region that defines the 3'-side of one of the strands constituting the specific region and the 5'-end of which comprises a nucleotide sequence complementary to an arbitrary region of a complementary strand synthesis reaction product obtained using the primer as a synthesis origin; and a nucleotide substrate;

under a condition that enables the synthesis of complementary strand using the first primer as an origin.

[15] The method according to [14], wherein the elements further comprise:

a third primer that becomes an origin of the complementary strand synthesis reaction, using the 3'-side of the region in the template to be annealed by the first primer as an origin; and a fourth primer that becomes an origin of the complementary strand synthesis reaction, using the 3'-side of the region in the template to be annealed by the second primer as an origin.

[16] The method according to [14]1, wherein the incubation is carried out in the presence of a melting temperature regulator.

[17] The method according to [16], wherein the melting temperature regulator is at least one of compounds selected from the group consisting of betaine, proline, dimethyl sulfoxide, and trimethylamine-N-oxide.

[18] A method for placing a region of a target template nucleic acid to be annealed by a primer that initiates a reaction of amplifying a template nucleic acid at a constant temperature, in a condition such that the region can undergo base pairing, wherein the method comprises the step of incubating a template double-stranded nucleic acid, an arbitrary primer, and a primer capable of amplifying the template nucleic acid at a constant temperature, in the presence of DNA polymerase, which catalyzes a complementary strand synthesis accompanying strand displacement, under a condition that ensures the synthesis of complementary strand, using the arbitrary primer as an origin.

In the present invention, a primer capable of amplifying a nucleic acid template at a constant temperature is used. The primer capable of amplifying the nucleic acid template at a constant temperature means a primer used for a method for amplifying nucleic acid without thermal cycling, using as a template a nucleic acid having a region to be annealed by the primer, which can undergo base pairing. Namely, the primer of the present invention is one for a reaction of amplifying a nucleic acid without thermal cycling. The primer of the present invention is not specifically limited, so long as it is a primer that enables isothermal nucleic acid amplification. Accordingly, regardless of whether it can be used for a reaction that requires thermal cycling, any primer that enables isothermal nucleic acid amplification is included in the primer of the present invention. As described above, amplification has been reportedly carried out at a constant temperature utilizing the primers for PCR. However, since the method cannot attain amplification of a practical level, the primer for PCR cannot be said to be a primer that enables isothermal nucleic acid amplification. In particular, amplification of a template nucleic acid can be carried out utilizing a method capable of continuous complementary strand synthesis that does not require thermal cycling. The primers used for such a method are desirable as primers of the present invention.

In a preferred embodiment, the method for amplifying nucleic acid utilizes a reaction principle (LAMP method) which repeats the complementary strand synthesis reaction by self annealing of the 3'-terminal region that is used as a template by itself, as described below. Additionally, the SDA method which is a known nucleic acid amplification reaction, can be used. In the present invention, the phrase "a region that can undergo base pairing" means a region that is not accompanied by a complementary strand. Accordingly, it includes not only a single-stranded nucleic acid that is produced by denaturing a double-stranded nucleic acid, but also a single-stranded nucleic acid contained in a double-stranded nucleic acid partially having single-stranded portions.

Further, in the present invention, the nucleic acid can be a DNA, an RNA, or a chimera molecule thereof. The nucleic acid can be a natural nucleic acid or an artificially synthesized nucleic acid. Further, a nucleotide derivative having a partial or entirely complete artificial configuration may be included in the nucleic acid of the present invention, so long as it can undergo base pairing. An example of such a molecule is, for example, a polynucleotide derivative in which a backbone is formed by phosphothioate bonds. The number of nucleotides constituting the nucleic acid used in the present invention is not limited. Herein, the term nucleic acid has the same meaning as the term polynucleotide. On the other hand, the term oligonucleotide used herein means a particular polynucleotide having a smaller number of constituting nucleotides. In general, an oligonucleotide means a polynucleotide having 2 to 100 and more usually 2 to 50 nucleotides, but it is not restricted by these numbers.

As used herein, the target nucleotide sequence means the nucleotide sequence of the nucleic acid to be synthesized. Namely, a nucleotide sequence constituting the nucleic acid to be synthesized in the present invention is the target nucleotide sequence. Further, when the amplification of the nucleic acid is carried out based on the nucleic acid synthesis method of the present invention, a nucleotide sequence that constitutes the nucleic acid to be amplified is the target nucleotide sequence. In general, the nucleotide sequence of a nucleic acid is described from the 5'-side to the 3'-side of the sense strand. The target nucleotide sequence of the present invention includes not only the sense strand but also the nucleotide sequence of the complementary strand thereof, i.e. the antisense strand. More specifically, the term "target nucleotide sequence" refers to at least either the nucleotide sequence to be synthesized or its complementary strand.

The nucleic acid synthesis method of the present invention uses a double-stranded nucleic acid as a template. In the context of the present invention, the double-stranded nucleic acid is a nucleic acid in the form of the hybridized complementary strands, at least in a region comprising a nucleotide sequence complementary to a primer that is used as a synthesis origin of the complementary strand synthesis. Accordingly, a target nucleotide sequence that is not double-stranded in parts is included in the double-stranded nucleic acid used in the present invention. Further, the double-stranded nucleic acid used in the present invention can be not only a dimer, but also a hybridization product of two or more of single-stranded nucleic acids, so long as it satisfies the above-mentioned condition. Furthermore, it can be a hair-pin loop constituted by a single-stranded polynucleotide which contains a complementary nucleotide sequence in the molecule. The double-stranded nucleic acid to be used in the present invention includes, for example, cDNA, genome DNAs, and DNA-RNA hybrids. In addition, various vectors in which these DNAs have been inserted can also be used as the double-stranded nucleic acid used in the present invention. The double-stranded nucleic acid used in the present invention may be purified or crude nucleic acid. Moreover, the method of the present invention is also applicable to nucleic acid in cells (in situ). In-situ genomic analysis can be performed using as the template a double-stranded nucleic acid in cells.

When a cDNA is used as the template in the present invention, the cDNA synthesis can be carried out under the same conditions as for the nucleic acid synthesis according to the present invention. When a first strand of cDNA is synthesized using RNA as the template, a double-stranded nucleic acid in the form of DNA-RNA hybrid is formed. Using the thus-obtained double-stranded nucleic acid as the template, the method for synthesizing nucleic acids according to the present invention can be conducted. When the DNA polymerase used in the nucleic acid synthesis method of the present invention has a reverse transcriptase activity, the nucleic acid synthesis can be performed using it as a single enzyme under the same condition. For example, Bca DNA polymerase is a DNA polymerase having strand displacement activity as well as reverse transcriptase activity. As a matter of course, the method for synthesizing nucleic acids according to the present invention can also be used after the formation of complete double-stranded cDNA by the second strand synthesis.

Polymerase that catalyzes the complementary strand synthesis reaction accompanying strand displacement is employed in the nucleic acid synthesis of the present invention. The complementary strand synthesis reaction accompanying strand displacement used herein means the following reaction. Namely, a reaction in which when the template for the complementary strand synthesis reaction, using a primer as a synthesis origin, is hybridized with another polynucleotide and in the form of a double strand, the complementary strand synthesis proceeds while separating the polynucleotide from the template, is called the strand displacement complementary strand synthesis reaction. At this time, the phosphodiester bonds in the polynucleotide separated is usually maintained. Accordingly, the polynucleotide thus formed has a length corresponding to that of the synthesized complementary strand and can undergo base pairing.

The same type of DNA polymerases as those used for SDA and such can be used as a polymerase that catalyzes the strand displacement complementary strand synthesis. The known unique polymerases synthesize complementary strands by, if a double-stranded region exists at the 5'-side of the template, displacing the double-stranded region using a primer complementary to a 3'-side region of a certain nucleotide sequence as the synthesis origin. According to the present invention, a substrate required for the complementary strand synthesis is further used.

An arbitrary primer is mixed with the double-stranded nucleic acid in the present invention, and the mixture is incubated under conditions that ensure the synthesis of the complementary strand using the primer as the origin. The arbitrary primer of the present invention allows the region to which a primer for amplification reaction of nucleic acid at a constant temperature will anneal to become ready for base pairing. Thus, the arbitrary primer must be able to initiate the complementary strand synthesis, using the complementary strand of the nucleotide strand as template, to which a primer for amplification reaction anneals, of the template double-stranded nucleic acid. Further, the strand extension in the complementary strand synthesis using the arbitrary primer of the present invention as the synthesis origin should proceed toward the region to which a primer for amplification reaction anneals. In other words, the primer can provide the synthesis origin in an arbitrary portion of the region, which region serves as the template in a complementary strand synthesis using the primer for amplification reaction as the origin. The arbitrary primer may comprise a nucleotide sequence complementary to arbitrary regions, so long as it meets the above criterion. For example, one of the primer set for the amplification reaction can also be used as the arbitrary primer. The use of the primer is one of the preferred embodiments of the present invention, due to the reduced number of necessary reaction components.

Base pairing with primer for amplification reaction can be ensured by displacing one of the two strands of the double-stranded nucleic acid in complementary strand synthesis using the arbitrary primer as the origin. By choosing such parameters, the synthesis reaction can proceed without changing temperature, which is one of the great features of the present invention Conditions which allow to proceed the complementary strand synthesis reaction by an arbitrary primer using a double-stranded nucleic acid as a template are practically the same as those required for the following multiple to proceed:

i) providing the synthesis origin by an arbitrary primer to a template double-stranded nucleic acid; and ii) proceeding with complementary strand synthesis reaction using the synthesis origin.

It was believed that a primer could provide a synthesis origin to a nucleic acid strand only if the region to which the primer anneals was single-stranded. Thus, previously, when a double-stranded nucleic acid was used as a template, the nucleic acid was subjected to denaturation, a step that converts the nucleic acid to single strands prior to primer annealing. However, a synthesis origin can be provided by incubating a template with a primer under a condition whereby the double strand is destabilized by a certain means yet not completely converted to single strands. An example of such a double strand destabilizing condition involves heating the double-stranded nucleic acid almost to the melting temperature (hereinafter abbreviated as Tm). Alternatively, the addition of a Tm regulator is also effective.

The reaction, comprising a series of steps, is carried out in the presence of buffer, providing a pH suitable for the enzyme reaction as well as salts required for annealing of primer and maintaining the catalytic activity of the enzyme, preservatives for the enzyme, and in addition, if needed, a melting temperature (Tm) regulator, and such. The buffer, with a buffering action in a range from the neutral to weak alkaline pH, such as Tris-HCl, is used in the present invention. The pH is adjusted depending on the type of DNA polymerase used. Examples of salts to be added to maintain the enzyme activity and to modify the melting temperature (Tm) of nucleic acid include KCl, NaCl, $(NH_4)_2SO_4$, etc. The enzyme preservatives include bovine serum albumin and sugars.

Further, typical melting temperature (Tm) regulators include betaine, proline, dimethylsulfoxide (hereinafter abbreviated as DMSO), formamide, and trimethylamine-N-oxide (TMANO). When a melting temperature (Tm) regulator is used, annealing of the above-mentioned oligonucleotide can be regulated within a limited temperature range. Moreover, betaine (N,N,N-trimethylglycine) and tetraalkylammonium salts effectively contribute to the improvement of the efficiency of strand displacement due to its isostabilizing action. The addition of betaine, at a concentration of about 0.2 to about 3.0 M, preferably about 0.5 to about 1.5 M, to the reaction solution is expected to enhance the amplification of nucleic acids of the present invention. Since these melting temperature regulators decrease the melting temperature, a condition giving desired stringency and reactivity is empirically chosen by considering reaction conditions, such as salt concentration and reaction temperature.

Temperature conditions suitable for enzyme reactions can be readily chosen by utilizing a Tm regulator. Tm varies, depending on the relation of the primer and target nucleotide sequence. Thus, it is preferable to adjust the amount of a Tm regulator so that the conditions that maintain the enzyme activity are consistent with the incubation conditions that meet the criterion of the present invention. Based on the disclosure of the present invention, those skilled in the art can readily choose proper amounts of a Tm regulator to be added, depending on the primer nucleotide sequence. For example, Tm can be determined based on the length of the annealing nucleotide sequence, the GC content, the salt concentration, and the concentration of the Tm regulator.

Annealing of a primer to a double-stranded nucleic acid under such conditions is presumed to be unstable. However, the complementary strand synthesis proceeds using the unstable primer as the synthesis origin when the DNAs; are incubated with a polymerase that catalyzes the strand displacement complementary strand synthesis. As the complementary strand synthesis proceeds, hybridization between the synthesized complementary strand and the template nucleic acid becomes more stable over time. The DNA polymerases listed below can catalyze the complementary strand synthesis using a primer as synthesis origin to the template double-stranded nucleic acid.

A DNA polymerase catalyzing strand displacement complementary strand synthesis reaction plays a central role in the method for synthesizing a nucleic acid according to the present invention. Such DNA polymerases include those listed below. In addition, various mutants of these enzymes can be used in the present invention, so long as they have the activity of sequence-dependent complementary strand synthesis and the strand displacement activity. Such mutants include truncated enzymes having only the structures with the catalytic activity or mutant enzymes whose catalytic activity, stability, or thermal stability has been modified by amino acid mutations, and such.

Bst DNA polymerase
Bca(exo-) DNA polymerase
Klenow fragment of DNA polymerase I
Vent DNA polymerase
Vent(Exo-) DNA polymerase (exonuclease activity-free Vent DNA polymerase)
DeepVent DNA polymerase
DeepVent(Exo-) DNA polymerase (exonuclease activity-free DeepVent DNA polymerase)
Φ29 phage DNA polymerase
MS-2 phage DNA polymerase
Z-Taq DNA polymerase (Takara Shuzo)
KOD DNA polymerase (TOYOBO)

Among these enzymes, Bst DNA polymerase and Bca (exo-) DNA polymerase are particularly preferred, because they have a high degree of thermal stability and high catalytic activity. According to the present invention, the step of using a primer as synthesis origin to a double-stranded nucleic acid and complementary strand synthesis reaction are conducted under the same conditions. Since such reactions often requires some heating, the use of thermostable enzymes is preferred. The reaction can be achieved under a wide variety of conditions using thermostable enzymes.

For example, Vent(Exo-) DNA polymerase is a highly thermostable enzyme that has strand displacement activity. It has been reported that the addition of a single strand-binding protein accelerates the reaction of strand displacement complementary strand synthesis by DNA polymerase (Paul M. Lizardi et al., Nature Genetics 19, 225-232, July, 1998). By applying the method to the present invention, acceleration of complementary strand synthesis is expected by the addition of single strand-binding protein. When Vent(Exo-) DNA polymerase is used, T4 gene 32 is effective as the single strand-binding protein.

When a DNA polymerase lacking 3'-5' exonuclease activity is used, a phenomenon wherein the complementary strand synthesis is not terminated even when the reaction reaches the 5'-end of the template and an extra nucleotide is added to the synthesized strand is known in the art. Such a phenomenon is not preferable in the present invention, because the next complementary strand synthesis initiates from the synthesized 3'-end complementary strand sequence. However, the nucleotide added to the 3'-end by the DNA polymerase is nucleotide "A" with high probability. Thus, a sequence for complementary strand synthesis should be selected so as to initiate synthesis from the 3'-end from A to avoid problems by the erroneous addition of a single-dATP nucleotide. Alternatively, even when the 3'-end protrudes during complementary strand synthesis, it can be digested to a blunt end by a 3'→5' exonuclease activity. For example, the natural Vent DNA polymerase, which has such activity, can be used in combination with Vent(Exo-) DNA polymerase to overcome the problem.

Unlike the DNA polymerases described above, DNA polymerases, such as Taq polymerase PCR which are routinely used in PCR and such, exhibit substantially no activity of strand displacement under typical conditions. However, such DNA polymerases can be used for the present invention, so long as they are used under conditions that ensure strand displacement.

A phenomenon wherein a complementary strand is synthesized by incubating a primer under a condition that the double-stranded nucleic acid becomes unstable, has been reported (Published Japanese Translation of International Publication No. Hei 11-509406; WO97/00330). However, only a trace amount of the synthesis product is expected to be actually produced under the condition reported. Although in principal it is possible to carry out the complementary strand synthesis using a primer as the synthesis origin by utilizing the destabilization of the double-stranded nucleic acid, the reaction is not as efficient as the reaction that uses a single-stranded nucleic acid as a template. When combined with a complementary strand synthesis reaction which requires a temperature change, such as the PCR method, the efficiency of the complementary strand synthesis reaction, which utilizes the destabilization of the double-strand, influences all of the complementary strand synthesis reactions; therefore, it is difficult to attain a practically usable reaction efficiency. This is believed to be the cause for insufficient amplification efficiency in the known methods.

On the other hand, the present invention is based on a finding whereby the low efficiency of the complementary strand synthesis based on the destabilization of the double-strand nucleic acid can be compensated by applying the complementary strand synthesis reaction based on the destabilization of the double-stranded nucleic acid to the nucleic acid amplification reaction that provides a region to be annealed by the primer for the amplification reaction that originally proceeds at a constant temperature. Since the present invention utilizes a nucleic acid amplification reaction that proceeds at a constant temperature, if a region to which a primer anneals is placed in a condition that ensures base pairing, the subsequent complementary strand synthesis reaction, which does not require the destabilization of the double-strand, proceeds. Accordingly, the influence of the low efficiency of the complementary strand synthesis reaction based on the destabilization of the double-strand can be minimized. A practically usable level of the synthesis efficiency is achieved for the first time by the combination of the two methods. In other word, the complementary strand synthesis reaction based on the destabilization of the double-strand is useful as the reaction for supplying a region to be annealed by the primer for the nucleic acid amplification reaction that proceeds isothermally. To the contrary, it is difficult to apply it to a nucleic acid amplification reaction that requires thermal cycling.

In the isothermal method of amplifying nucleic acid according to the present invention, for example, it is desirable that the 3'-end is annealed to itself and is used as a template for the complementary strand synthesis reaction. Namely, the main characteristic of the present invention is that a temperature change is not required and the best use of it is realized in particular when the primer as described below is used. The nucleic acid amplification method using a primer having a specific configuration was conceived by the present inventors. Hereinafter, the method is described as the LAMP (Loop-mediated isothermal amplification) method. According to the LAMP method, the 3'-end of a template polynucleotide anneals to itself to serve as the origin of complementary strand synthesis, and a primer that anneals to the thus-formed loop is used to enable the isothermal complementary strand synthesis reaction. The present inventors found that denaturing of a double-stranded template is not needed.

The present invention relates to a nucleic acid synthesis method that uses a primer that can amplify the nucleic acid isothermally, the primer being an oligonucleotide constituted by at least two regions, X2 and X1c, where X1c is connected to the 5'-side of X2.

Herein, X2 is defined as a region having a nucleotide sequence complementary to an arbitrary region X2c of the nucleic acid that has a specific nucleotide sequence.

Further, X1c is defined as a region having a nucleotide sequence substantially identical to an arbitrary region at the 5'-side of the region X2c of the nucleic acid having a specific nucleotide sequence.

The primer is utilized as a first primer and a second primer in the explanation given below. The first primer anneals to the extended product synthesized using the second primer as an origin to serve as the origin of the complementary strand synthesis reaction and vice versa. The synthesis product prepared by the nucleic acid synthesis method, which uses the primer as the synthesis origin, enables the nucleic acid amplification which will be mentioned below. The present invention relates to a method for synthesizing nucleic acid in which a plural number of nucleotides, constituting a specific region of a double-stranded template nucleic acid that is constituted by complementary nucleotide sequences, are connected on a single-strand, wherein the method comprises the following steps. Herein, a condition that a certain nucleotide sequence 1 and at least one nucleotide sequence 2 complementary thereto exist on the identical strand, is referred to as a condition containing a plural number of complementary nucleotide sequences on a single-strand.

a) incubating a template double-stranded nucleic acid and an arbitrary primer in the presence of DNA polymerase, which catalyzes a complementary strand synthesis reaction accompanying strand displacement, under a condition that ensures the synthesis of complementary strand using the primer as an origin, such that a region of the target template nucleic acid to be annealed by a primer capable of amplifying the template nucleic acid at a constant temperature, is placed in a condition wherein the region can undergo base pairing;

b) annealing the second primer to the region obtained in the step a), which can undergo base pairing, and carrying out the synthesis of complementary strand using the second primer as an origin, wherein the 3'-end of the second primer anneals to a region that defines the 3'-side of one of the strands constituting the specific region and the 5'-end of the second primer comprises a nucleotide sequence complementary to an arbitrary region of a complementary strand synthesis reaction product obtained using the primer as an origin;

c) placing a region of the extended product of the second primer synthesized in the step b), to which a first primer will anneal, in a condition wherein it can undergo base pairing;

d) annealing the first primer to the region obtained in the step c), which can undergo base pairing, and carrying out the synthesis of complementary strand using the first primer as an origin, wherein the 3'-end of the first primer anneals to a region that defines the 3'-side of said region in the extended product obtained using the second primer as an origin; and e) allowing self annealing at the 3'-end of the extended product of the first primer synthesized in the step d), carrying out the synthesis of complementary strand using the extended product as a template, and obtaining nucleic acid in which a plural number of nucleotides, constituting the specific region, are connected on single strand.

Among the above-mentioned reactions, only step a) is achieved by the destabilization of the double-stranded nucleic acid. The extended product of the primer for amplification reaction (namely, the second primer), which has obtained a region to be annealed in this step, is utilized as the template in the subsequent reaction. It should be noted that since the DNA polymerase catalyzing the strand displacement complementary strand synthesis reaction is used, not only together with the primer for amplification reaction, but also throughout the complementary strand synthesis in the present invention, the double-stranded configuration appearing in the preceding direction of the complementary strand synthesis reaction does not obstruct the reaction if only the annealing of the primer is achieved.

Furthermore, in the present invention, the reaction following this step originally proceeds at a constant temperature and does not depend on a complementary strand synthesis that utilizes the destabilization of the double-stranded nucleic acid with a poor efficiency. Namely, the nucleic acid amplification reaction, which proceeds at a constant temperature, is initiated following the complementary strand synthesis using the primer used in the step a) as a synthesis origin.

Even after the nucleic acid amplification reaction that proceeds isothermally is initiated, a primer for the target nucleotide sequence which exists in the reaction system may possibly cause the synthesis of complementary strand, based on the destabilization of the double-stranded nucleic acid. The possibility of the occurrence of such reaction cannot be denied, and it is needless to say that the occurrence of such reaction contributes to the improvement of the whole reaction efficiency. The complementary strand synthesis reaction based on the destabilization of the double-stranded nucleic acid, which is concurrently occurs during the amplification reaction, is not essential in the nucleic acid amplification reaction according to the present invention.

It is advantageous to utilize an outer primer in the step c) of the above-mentioned reaction. Herein, the outer primer provides the origin of the complementary strand synthesis reaction that proceeds towards a primer that anneals to the target nucleotide sequence (this primer is called an inner primer, contrary to the outer primer). Accordingly, the region to which the outer primer anneals is the region of the 5'-side (3'-side in a template) of the inner primer. As the outer primer, an oligonucleotide comprising a nucleotide sequence that functions as a primer at least at its 3'-side can be used. The first primer and the second primer correspond to the inner primer in this example.

On the other hand, the inner primer contains at its 3'-end the nucleotide sequence of the double-stranded nucleic acid template, which is complementary to a nucleotide sequence of a region to be synthesized. The inner primer is usually used as a set of two primers. However, if the region to be synthesized contains repeats of the identical nucleotide sequence, the two primers may comprise the identical nucleotide sequence. The primer set is designed such that one of the inner primers can anneal to the extended product from another inner primer. When at least the nucleotide sequences at both ends of the region to be amplified are known, a method of determining the nucleotide sequence used as a primer is well known.

If the inner primers are primers whose 3'-sides can anneal to the target nucleotide sequence, an arbitrary nucleotide sequence can be added to the 5'-side of the inner primer. The fact that an arbitrary sequence can be added to the 5'-side of the inner primer gives many variations to the nucleic acid synthesis method of the present invention. The specific examples are described below.

The inner primers in the present invention can be nested. Namely, the second inner primer set, which can anneal to the second target nucleotide sequence, can be further combined with the first inner primer set, which can anneal to the first target nucleotide sequence. In this combination, the first target nucleotide sequence is contained within the second target nucleotide sequence. When the inner primers are nested, the outer primers are designed so as to anneal to the 5'-side of the second inner primers (3'-side of the template).

The inner primers usually comprise a combination of two primers, while the number of the outer primers can be arbitrary. In general, the outer primer of the present invention comprises two primers that provide the origins of the complementary strand synthesis reaction that proceeds towards the regions to which the respective inner primers anneal. However, even if the outer primers are only applied to either of the inner primers, the method of the present invention can be carried out. Alternatively, a plural number of outer primers can be combined with one inner primer. At all times, when the complementary strand synthesis that proceeds towards the region to which the inner primers anneal is accompanied, the product of the complementary strand synthesis reaction using the inner primers as the synthesis origin can be efficiently generated.

The complementary strand synthesis driven by the outer primers in the present invention is designed to be initiated subsequent to synthesis of the complementary strand using the inner primers as the synthesis origin. The simplest means to achieve this occurs when the concentration of the inner primers is higher than that of the outer primers. Specifically, the complementary strand synthesis from the inner primers can be predominantly carried out when the difference of the concentration of the primers is usually about 2 to 50-fold, and preferably about 4 to 10-fold. Further, the timing of the complementary strand synthesis reaction can be controlled by setting the melting temperature (Tm) of the outer primers lower than Tm of the inner primers. The melting temperature (Tm) can be theoretically calculated, based on the length of the complementary strand which is annealed and the combination of the nucleotides constituting the base pairing, when all other conditions are constant. Accordingly, those skilled in the art can easily derive a desirable reaction condition from the disclosure of the present specification.

Further, a phenomenon called a contiguous stacking can be applied to adjust the timing of annealing of the outer primers. The contiguous stacking is a phenomenon in which an oligonucleotide that cannot independently anneal is able to anneal when it is placed adjacent to a double-stranded portion (Chiara Borghesi-Nicoletti et al., Bio Techniques 12, pp. 474-477 (1992)). Namely, the outer primers are placed adjacent to the inner primers and are designed such that they cannot independently anneal under the incubation condition. Thus, only if the inner primers anneal can the outer primers anneal. Therefore, the annealing of the inner primers is inevitably predominated. Based on the principle, an example of setting the nucleotide sequence of the primer oligonucleotide necessary for a series of reactions is described in Example.

In the explanation described below, X2 and X1c in one of the inner primers are temporarily referred to as F2 and F1c, and X2 and X1c in the other inner primer are referred to as R2 and R1c. The inner primers used for explanation are temporarily named as FA and RA. One of FA and RA is the first primer of the present invention, and the other functions as the second primer. The regions which constitute FA and RA are as follows:

|    | X2 | X1c |
|----|----|-----|
| FA | F2 | F1c |
| RA | R2 | R1c |

In the nucleic acid amplification method of the present invention, through the above-mentioned steps a) to c), it is important to produce a nucleic acid that has at its 3'-end the region F1, which can anneal to the portion F1c on the same strand, form a loop containing the region F2c, and undergo base pairing by annealing of the region F1 to F1c on the same strand. Such nucleic acid configuration can be provided by the nucleic acid synthesis reaction based on the present invention utilizing the inner primers having the following configuration. The details of the reaction are as mentioned above.

Namely, the inner primers which are used for the nucleic acid amplification reaction of the present invention are constituted by at least the above-mentioned two regions X2 and X1c, and comprise the oligonucleotide in which X1c is connected with the 5'-side of X2.

Herein, the nucleic acid having a specific nucleotide sequence which determines the configuration of the inner primers of the present invention means a nucleic acid which becomes the template when the inner primers of the present invention are utilized as the primer. When the nucleic acid amplification is carried out based on the synthesis method of the present invention, the nucleic acid having a specific nucleotide sequence is a double-stranded nucleic to be amplified or its derivative. The double-stranded nucleic acid having a specific nucleotide sequence means a nucleic acid in which at least a portion of the nucleotide sequence is clarified or whose sequence can be presumed. The portion whose nucleotide sequence should be clarified is the above-mentioned region X2c and the region X1c at its 5'-side.

The two regions may be linked to each other or may exist separately. The state of the loop portion formed by self-annealing of the product nucleic acid depends on the relative position of the two regions. Preferably, the two regions are not unnecessarily separated, such that self-annealing of the product nucleic acid more preferentially achieved than annealing of two molecules. Thus, a preferred length of the spacer nucleotide sequence between the two regions is typically 0 to 500 nucleotides. However, in some cases, regions existing too close to each other may be disadvantageous for forming a desirable self-annealing loop. More specifically, it is desirable that the loop have a structure that enables annealing of a new primer and a smooth start to strand displacement complementary strand synthesis reaction. Thus, more preferably, the primers are designed such that the distance between the region X2c and the region X1c located at its 5'-side is about 0 to 100 nucleotides, further preferably about 10 to 70 nucleotides. The distance values enumerated herein do not contain the lengths of X1c and X2. The nucleotide length of the loop portion further includes the length corresponding to X2.

Further, the terms "identical" and "complementary" as used herein to characterize the nucleotide sequence which constitutes the primer used for the present invention encompass cases that are not completely identical and not completely complementary. More specifically, a sequence identical to a certain sequence may also include a sequence complementary to a nucleotide sequence that can anneal to the certain sequence. On the other hand, a complementary sequence refers to a sequence that anneals under stringent conditions and provides the origin for complementary strand synthesis. In the present invention, the term "identical" means that the homology of the nucleotide sequence is, for example, 90% or more, usually 95% or more, and more preferably 98% or more. The term "complementary" refers to a nucleotide sequence identical to the complementary sequence. Namely, when the homology of the nucleotide sequence is, for example, 90% or more, usually 95% or more, and more preferably 98% or more to the complementary sequence, it can be said as "complementary". Further, when the complementary nucleotide sequence functions as the origin of the complementary strand synthesis, it is desirable that at least one nucleotide of the 3'-end coincides completely with the complementary sequence.

The regions X2 and X1c constituting the inner primer used in the present invention are typically arranged continuously, without overlapping each other. Alternatively, if X2 and X1c share a common nucleotide sequence, they may be placed so that they partly overlap each other. Without exception, X2 should be placed at the 3'-end to function as a primer. On the other hand, X1c is placed at the 5'-end as described below, to provide a function as a primer to the 3'-end of a complementary strand synthesized using X1c as the template. The complementary strand obtained using the oligonucleotide as the synthesis origin serves as the template of the reverse complementary strand synthesis in the next step, and finally the inner primer portion according to the present invention is also copied as the template to the complementary strand. The copied 3'-end contains the nucleotide sequence X1, and anneals to X1c located within the identical strand to form a loop.

The inner primer used in the present invention is an oligonucleotide that meets two requirements: (1) it has the ability to form a base pair complementary to a target nucleotide sequence, and (2) it provides an —OH group at the 3'-end of the base pair that serves as the origin of complementary strand synthesis. The backbone of the primer is not restricted to those composed of phosphodiester bonds. For example, the primer may comprise phosphothioate. Further, the nucleotide may be any nucleotide, so long as it forms a complementary base pair. In general, there are five types of naturally occurring nucleotides, namely A, C, T, G, and U; however, analogues such as bromodeoxyuridine, for example, are also included. The oligonucleotide used in the present invention serves not only as the synthesis origin but preferably acts also as the template of complementary strand synthesis.

The inner primer used in the present invention consists of nucleotides with appropriate length to enable base pairing with the complementary strand by maintaining required specificity under a given condition in various types of nucleic acid synthesis reactions described below. Specifically, the primer comprises 5 to 200 nucleotides, and more preferably 10 to 50 nucleotides. The minimal length of a primer recognized by known polymerases catalyzing sequence-dependent nucleic acid synthesis is around 5 nucleotides. Thus, the length of an annealing portion must be at least 5 nucleotides or longer. In addition, to ensure a high probability of nucleotide-sequence specificity it is preferred to use a primer comprising 10 nucleotides or more. On the other hand, an overlong nucleotide sequence is difficult to chemically synthesize. Thus, the above-mentioned length of primers is exemplified as the preferred range. The exemplified length of primers corresponds only to the portion annealing to the complementary strand. The inner primer of the present invention comprises at least two regions, X2 and X1c. Thus, the exemplified length of primers above should be understood as a length corresponding to the length of each region constituting the inner primer.

Further, the inner primer used in the present invention can be labeled with known labeling substances. Such labeling substances include ligands with binding capacity, such as digoxin and biotin; enzymes; fluorescent substances; luminescent substances; and radioisotopes. In addition, techniques are known for converting nucleotides in inner primer to fluorescent analogues (WO 95/05391; Proc. Natl. Acad. Sci. USA, 91, 6644-6648, 1994).

Further, the inner primer used in the present invention can be immobilized on a solid phase. Alternatively, an arbitrary portion of the inner primer may be labeled with a ligand that has binding capacity, such as biotin, and then can be indirectly immobilized via a binding partner, such as immobilized avidin. When an immobilized inner primer is used as the synthesis origin, the synthesized nucleic acid product is immobilized on a solid phase, and thus can be readily separated. The separated product may be detected by nucleic acid-specific indicators or by further hybridizing a labeled probe. Alternatively, a nucleic acid fragment of interest can be recovered by digesting the nucleic acid with an arbitrary restriction enzyme.

The term "template" as used herein refers to nucleic acids that serve as a template in the synthesis of a complementary strand. Although a complementary strand having a nucleotide sequence that is complementary to a template is a strand corresponding to the template, the relationship between the two is merely relative. Specifically, a strand synthesized as a complementary strand has the ability to function as a template. In other words, a complementary strand can also serve as a template.

The inner primer in the present invention may contain regions additional to the above-mentioned two regions. Specifically, X2 and X1c are placed at the 3'-end and 5'-end, respectively, and an arbitrary sequence can be placed between the two regions. Such an arbitrary sequence includes, for example, a restriction enzyme recognition sequence, a promoter recognized by RNA polymerase, a DNA encoding ribozyme, etc. The single-stranded nucleic acid, the synthesis product of the present invention, wherein complementary nucleotide sequences are connected, can be digested to two double-stranded nucleic acids with identical length by inserting a restriction enzyme recognition sequence. By inserting a promoter sequence recognized by RNA polymerase, the synthesized product of the present invention can be transcribed into RNA using the product as the template. Furthermore, by additionally arranging a DNA encoding a ribozyme, it is possible to establish a self-cleaving system for the transcripts. All of the additional nucleotide sequences mentioned above function only when the sequences are formed to double-stranded nucleic acids. Accordingly, these sequences do not function in the single-stranded nucleic acid of the present invention that is in the form of a loop. The additional sequences function for the first time only after the nucleic acid extension proceeds and the sequence anneals to a complementary nucleotide sequence without forming any loop.

When the inner primers used in the present invention are combined with a promoter in the direction which enables the transcription of the region synthesized, the reaction product according to the present invention, which has the identical nucleotide sequence repeatedly, realizes a highly efficient transcription system. The translation to protein is also possible by combining the transcription system with an appropriate expression system. Namely, it can be applied to transcription and translation to protein in a bacterium or an animal cell, or in vitro.

Various primers used in the present invention can be chemically synthesized. Alternatively, a natural nucleic acid may be digested by restriction enzyme and the like to modify or connect so as to contain the above-mentioned nucleotide sequence.

The basic principle of the amplification reaction for double-stranded nucleic acids by the combined use of the above-mentioned inner primers, FA and RA, and DNA polymerase having strand displacement activity is described below referring to FIGS. 1 to 4. According to the examples, the amplification primer set consists of the inner primers, FA and RA, and further, RA serves as an arbitrary primer in the present invention.

The above-mentioned arbitrary primer (RA in FIG. 1-(1)) first anneals to X2c (corresponding to R2c) on the template double-stranded nucleic acid to serve as the origin of complementary strand synthesis. Under such conditions, the double-stranded nucleic acid is unstable and the primer directly serves as the origin of complementary strand synthesis on the double-stranded nucleic acid. In FIG. 1-(2), the complementary strand synthesized using RA as the origin displaces one of the strands of the template double-stranded nucleic acid, and F2c, which is the region annealing with the primer for amplification reaction FA, becomes ready for base pairing (FIG. 1-(2)).

A complementary strand synthesis is conducted by annealing FA to the region F2c which is ready for base pairing. Herein, an outer primer F3, which initiates complementary strand synthesis from the 5'-side of FA (3'-side of template), also anneals to the region (FIG. 2-(4)). The outer primer is designed so as to initiate the synthesis of complementary strand on the 5'-side of each inner primer (3'-side of template). The outer primer further has a higher Tm and is used at a lower concentration than that of the inner primers. Thus, the outer primer always initiates a complementary strand synthesis with a lower probability as compared with the inner primers. As a result of complementary strand synthesis using the outer primer F3 as the origin, the extended product synthesized using the inner primer FA as the origin is displaced and released as a single strand (FIG. 2-(5)). Using this single strand as the template, RA and the outer primer, R3, corresponding to RA anneal to each other and initiate complementary strand synthesis (FIG. 3-(6)). As a result, the extended products from RA have a structure with which the 3'-end F1 can intramolecularly anneal with itself (FIG. 3-(8)). In FIG. 3-(6), the 5'-end of the strand is annealed intramolecularly to itself. However, the amplification reaction cannot be initiated with this structure, since the 5'-end does not serve as the origin of complementary strand synthesis. The amplification reaction is initiated only when a complementary strand to the strand shown in FIG. 3-(6) is synthesized, and, thereafter, a structure which anneals to itself at the 3'-end thereof is provided (FIG. 3-(8)). These reaction steps may be referred to as preliminary steps for the amplification reaction of the present invention.

Nucleic acid amplification according to the present invention is specifically described below, with reference to the schematic illustration depicted in the Figures. The self-annealed 3'-end F1 (FIG. 3-(8)) serves as the origin of complementary strand synthesis. Annealing to the 3'-end occurs between F1 and F1c, and thus, there is the possibility that the annealing competes with FA, that also contains F1c. However, in actuality, the complementary nucleotide sequences F1/F1c which exist in a neighboring region on an identical strand preferentially anneal to each other. Thus, the reaction of complementary strand synthesis using its own strand as the template is preferentially initiated. The nucleic acid in which the target nucleotide sequence has been connected on a single strand is synthesized through this reaction. Further, F2c, to which the inner primer FA can anneal, is present in a loop forming region that is formed by the self-annealing of the 3'-end F1. After FA anneals to this portion, complementary strand synthesis is initiated (FIG. 3-(8)). Complementary strand synthesis from FA annealed to the loop displaces the products of complementary strand synthesis initiated from the 3'-end using itself as the template, and again the 3'-end is allowed to become ready for self-annealing (FIG. 4-(9)). The subsequent reaction comprises alternating steps of complementary strand synthesis using the 3'-end of itself as the origin and its own strand as the template, and complementary strand synthesis using the loop portion as the origin and the inner primer FA or RA as the origin. As described above, the nucleic acid amplification reaction comprises the alternate steps of repeated 3'-end extension, using its own strand as the template, and newly initiated extension from the primer annealing to the loop portion.

On the other hand, regarding the nucleic acid strand synthesized complementary to the single-stranded nucleic acid, that is extended using its own strand as the template, using the oligonucleotide annealing to the loop portion thereof as the origin, synthesis of a nucleic acid having plural complementary nucleotide sequences connected on a single strand also proceeds on the synthesized nucleic acid strand. Specifically, the complementary strand synthesis from the loop portion is completed, for example, when it reaches R1 as depicted in FIG. 4-(9). Then, another complementary strand synthesis is newly initiated using the 3'-end displaced by the nucleic acid synthesis as the origin (FIG. 4-(9)). Eventually, the reaction reaches the loop portion that has been the origin of synthesis in the previous steps to initiate the displacement again. Thus, the nucleic acid that initiated the synthesis from the loop portion is also displaced, and as a result the 3'-end R1 annealing on the strand itself is produced (FIG. 4-(11)). This 3'-end R1 initiates complementary strand synthesis after annealing to R1c present on the identical strand. When F in this reaction is considered as R and R as F, the reaction is the same as that depicted in FIG. 3-(8). Thus, the structure depicted in FIG. 4-(11) serves as a new nucleic acid that continues the self-extension process and synthesis of another nucleic acid.

As described above, according to the method of the present invention, the reaction that continuously provides nucleic acids that initiate another extension proceeds together with the elongation of a nucleic acid. As the nucleic acid is further extended, multiple loop-forming sequences are generated not only at the strand end but also within the identical strand. When these loop-forming sequences become ready for base pairing through the synthesis reaction which comprises strand displacement, the inner primers anneal to the loop-forming sequences and serve as synthesis origins for producing new nucleic acids. More efficient amplification is achieved by combining synthesis initiated from internal regions of the strand to the strand synthesis from the strand end. As described above, strand extension accompanying synthesis of new nucleic acids can be achieved by applying the LAMP method. Further, according to the LAMP method, the newly generated nucleic acids themselves extend, and result in a new generation of other nucleic acids. Theoretically, this series of reaction continues endlessly, and thus can achieve extremely efficient nucleic acid amplification. In addition, the method of the present invention can be conducted under an isothermal reaction condition.

Herein, the reaction product accumulated has a structure in which the nucleotide sequences between F1 and R1, and complementary sequences thereof, are connected in plural numbers. The region containing the nucleotide sequences of F2-F1 (F2c-F1c) or R2-R1 (R2c-R1c) is continued at both ends of the sequences of repeating units. For example, FIG. 4-(10) shows a state that the nucleotide sequences are connected in the order of (R2-F2c)-(F1-R2c)-(R1-F1c)-(F2-R2c) from the 5'-side. This is because the amplification reaction of the present invention proceeds based on a principle that amplification is initiated from F2 (or R2) using the inner primers as a synthesis origins, and successively, the product extends from F1 (or R1) by the complementary strand synthesis reaction using the 3'-end itself as a synthesis origin.

As the most preferable embodiment herein, the inner primers, FA and RA, are used as the oligonucleotides that anneal to a loop portion. However, the nucleic acid amplification according to the present invention can be carried out only when using both the oligonucleotide having these limited structure as well as an oligonucleotide capable of initiating the complementary strand synthesis from a loop. Namely, if only the 3'-end (which continues to extend) is displaced by the complementary strand synthesis from a loop, another loop portion is provided again. Since the complementary strand synthesis, which is initiated from a loop portion, uses a template nucleic acid in which plural complementary nucleotide sequences are connected on a single-strand, it is obvious that a desired nucleic acid of the present invention can be synthesized. However, the thus-synthesized nucleic acid forms a loop after displacement to perform the complementary strand synthesis, but has no 3'-end for forming the loop thereafter and thus cannot function as a new template. Accordingly, contrary to the case of using the nucleic acid which initiates the synthesis from FA or RA, exponential amplification cannot be expected. For that reason, the inner primers having structures like FA and RA are useful in the present invention for highly efficient nucleic acid synthesis.

A series of reactions proceed simply by adding the components below to the double-stranded nucleic acid which serves as a template and incubating them under conditions that ensure the annealing of the inner primers and the outer primers and the complementary strand synthesis reaction using these primers as origins. The incubation conditions are as previously described. In the present invention, the amplification reaction of the template nucleic acid is achieved by incubating the following elements at a lower temperature than that required to denature the double-stranded nucleic acid which serves as the template. At this time, the step of denaturing the template nucleic acid is unnecessary. Herein, the temperature required for denaturing the double-stranded nucleic acid means a temperature at which the template nucleic acid can be converted to a single strand after rapid cooling.

Four kinds of oligonucleotides:
FA,
RA,
Outer primer F3, and
Outer primer R3;
DNA polymerase catalyzing strand displacement complementary strand synthesis reaction;
Nucleotide as a substrate of DNA polymerase As described in the explanation of the reaction principle, when the above-mentioned FA and RA are used as the inner primers, the nucleic acid synthesis method of the present invention, using the double-stranded nucleic acid as a template, is necessary for a reaction using as a template a nucleic acid derived from a sample. When the inner primers having specific structures like FA and RA are applied to the nucleic acid synthesis method of the present invention, the 3'-end of the generated product anneals to itself and serves as the origin of synthesis for the complementary strand, using itself as a template. Further, a new primer anneals to the loop portion, formed by self annealing of the 3'-end of the above-mentioned product, which serves as a synthesis origin, and the strand displacement complementary strand synthesis reaction proceeds. These reactions proceed independent of the nucleic acid synthesis method according to the present invention using the double-stranded nucleic acid as a template.

Namely, when FA and RA are used as the inner primers, the nucleic acid synthesis reaction of the present invention using the double-stranded nucleic acid as a template constitutes an initial reaction. Accordingly, the initial reaction requires a conditions that ensure the annealing of the inner primers and the outer primers and the complementary strand synthesis reaction using these primers as origins. The subsequent reactions can be performed under more appropriate conditions. However, when a temperature change is required for that purpose, the advantage of the present invention, wherein the denaturing step is not required, cannot be fully exploited. Accordingly, in the present invention, it is preferable that not only the initial reaction, but also all subsequent reactions be carried out under preferable conditions.

In cases where FA and RA are used as the inner primers of the present invention, it is important to note that the series of reaction steps proceed only when the relative positions of the multiple regions are constantly maintained. Accordingly, non-specific synthesis accompanying non-specific complementary strand synthesis can be effectively prevented. Specifically, this aspect contributes to the reduction in the probability that the product will serve as a starting material in a subsequent step of amplification, even when some non-specific reaction occurs. Furthermore, the fact that process of the reaction is controlled by a plurality of different regions provides one with the flexibility to construct a detection system that ensures precise discrimination of similar nucleotide sequences.

The aspect of the invention can be utilized to detect a mutation of a gene. Four kinds of primers in total—two kinds of the outer primers and two kinds of the inner primers—are used in the embodiment of the present invention that uses outer primers. If the nucleotide sequences constituting six regions which are contained in four kinds of oligonucleotides and the target nucleotide sequence are not made as designed, either of the complementary strand synthesis reactions of the present invention is inhibited. In particular, the nucleotide sequences near the 3'-end of the respective oligonucleotides which serve as the origin of synthesis for the complementary strand and the nucleotide sequences near the 5'-end of the X1c region whose complementary nucleotide sequence serves as the synthesis origin, are important for the complementary strand synthesis. Thus, if the nucleotide sequence important for the complementary strand synthesis is designed so as to correspond to the mutation to be detected, the presence or absence of the mutation, such as the deletion and insertion of nucleotide(s) or gene polymorphism such as SNPs, can be detected by observing the product of synthesis reaction according to the present invention.

More specifically, when the nucleotide expected to have a mutation or polymorphism located near the 3'-end of the oligonucleotides that serve as the origin of the complementary strand synthesis or a newly synthesized complementary strand becomes a synthesis origin, the nucleotide sequences should be designed so as to be equivalent to the sequence in the vicinity of the 5'-end of the strand which serves as the template in the complementary strand synthesis. When mismatch exists at the 3'-end, which serves as the origin of the complementary strand synthesis, or near around it, the nucleic acid complementary strand synthesis reaction is remarkably inhibited.

According to the LAMP method, extensive amplification is not achieved when a reaction from the end structure of the product, which is produced at early stages of the reaction, is not repeated many times. Thus, even if erroneous synthesis occurs, extensive amplification will not be achieved with mismatches, because the complementary strand synthesis for the amplification is inhibited at some stage. As a result, the mismatches effectively suppress the amplification to give a correct result. Namely, the nucleic acid amplification using LAMP method has a nucleotide sequence checking-mechanism with a higher degree of perfection. These features give an advantage over methods, for example, such as PCR, wherein simply sequences between two regions are amplified.

Further, the region X1c, which is characteristic of the oligonucleotide used in the present invention, only serves as the origin when a complementary sequence is synthesized, and the complementary sequence anneals to the newly synthesized X1 within the identical sequence to carry out the synthesis reaction using the strand itself as the template. Therefore, the oligonucleotides of the present invention are free from forming loops, which is often a serious problem in prior art even if a so-called primer-dimer is generated. Accordingly, non-specific amplification due to a primer-dimer does not occur in the present invention, which contributes to the improvement of the reaction specificity.

Nucleic acid amplification can be efficiently carried out by setting the Tm of the outer primers so as to be (outer primers F3: F3c)≦(F2c/F2) relative to the inner primers FA. It is desirable to design the respective regions constituting FA so that the annealing between F1c and F1 occurs more predominantly than that between F2c and F2. They should be designed taking Tm, the constituting base, and the like into consideration. Further, since the annealing between F1c and F1 is an intermolecular reaction, it shall also be noted that the annealing predominantly proceeds with a high possibility. It is needless to say that the similar condition shall also be taken into consideration for designing RA, which anneals to the extended product of FA. An ideal reaction condition can be attained with strong probability by ensuring such relation.

In the present invention, the terms "synthesis" and "amplification" of the nucleic acid are used. Nucleic acid synthesis herein refers to the elongation of nucleic acids from an oligonucleotide which serves as the synthesis origin. A series of reactions, including the continuous reaction of formation of other nucleic acids and elongation of the formed nucleic acids in addition to synthesis, are collectively referred to as "amplification".

The region F1, which can be annealed to a portion F1c on the identical strand, is provided at 3'-end by using FA and RA as the inner primers. The annealing of the region F1 to the region F1c on the identical strand produces a single-stranded nucleic acid which can form a loop containing the region F2c that can then undergo base pairing. The single-stranded nucleic acid functions as an important starting substance in the subsequent nucleic acid amplification reaction. The single-stranded nucleic acid can also be supplied based on the following principle. Namely, the synthesis of complementary strand proceeds using a primer having the following structure as the inner primer:

5'-[region X1 that anneals to region X1c positioned in primer]—[loop forming sequence which is in a condition ensuring base pairing]—[region X1c]—[region having sequence complementary to template]-3'.

Two kinds of a nucleotide sequence complementary to F1 (the primer FA) and a nucleotide sequence complementary to R1c (the primer RA) are prepared for the region having a sequence complementary to a template. Further, the nucleotide sequence of the nucleic acid to be synthesized includes the nucleotide sequence from the region F1 to the region R1c and the nucleotide sequence from the region R1, which has a nucleotide sequence complementary to the nucleotide sequence, to the region F1c. On the other hand, X1c and X1, which can be annealed intermolecularly in the primer, can be an arbitrary sequence. However, it is desirable that the sequences of the region X1c/X1 differ from the primers FA and RA.

First, using an arbitrary primer, the region F2 of the double-stranded nucleic acid which becomes the template is placed in a condition that ensures base pairing. The primer FA is then annealed to, F2 which can undergo base pairing, and the synthesis of complementary strand is carried out. At this time, RA can be used as the arbitrary primer. Then, the region R2c of the thus-synthesized complementary strand is placed in a condition that ensures base pairing, and another primer is annealed to this region to prepare the origin of the complementary strand synthesis. Since the 3'-end of the synthesized complementary strand has a nucleotide sequence complementary to the primer FA which constitutes the 5'-end portion of the firstly synthesized strand, it has the region X1 at the 3'-end, which then anneals to the region X1c on the identical strand to form a loop. Thus, the 3'-end configuration which is characteristic of the present invention as described above is provided, and the subsequent reaction is the reaction system which has been previously shown as the most desirable embodiment. Note, the oligonucleotide that anneals to the loop portion has the region X2 complementary to the region X2c, which exists in the loop, at the 3'-end, and the region X1 at the 5'-end. In the previous reaction system, the loop configuration is provided to the 3'-end of the nucleic acid by synthesizing a strand complementary to the template nucleic acid using the primers FA and RA. The method effectively provides the terminal configuration, which is characteristic of the present invention, using a short primer. On the other hand, in the present embodiment, the entire nucleotide sequence of the loop is provided as a primer from the first, and the synthesis of a longer primer is required.

In addition, the principle of the present invention can also be applied to known nucleic acid amplification methods such as, for example, SDA and NASBA. In order to apply the principle of SDA to the present invention, the primer set for SDA, DNA polymerase catalyzing the strand displacement complementary strand synthesis reaction, a restriction enzyme, and a substrate necessary for the complementary strand synthesis (including thionucleotide for giving nuclease resistance), are incubated together with the double-stranded nucleic acid which becomes the template under the above-mentioned conditions of the present invention. When either of the primers for SDA initiates the complementary strand synthesis by the destabilization of the double-strand, the region to which another primer should anneal in the substituted template nucleic acid becomes in a condition ensuring base pairing. Then, the annealing of the primers and the synthesis of the complementary strand to the template nucleic acid are carried out.

Next, the annealing of the outer primers to the primer and the synthesis of the complementary strand occur, and the complementary strand previously synthesized from the primer for SDA is substituted to generate a single-stranded nucleic acid. Further, the complementary strand synthesis using the above-mentioned arbitrary primer proceeds in the 5'-side direction of the template nucleic acid. Accordingly, not only the region to which the primer for SDA should anneal, but also the region to which the outer primer should anneal, become in a condition that ensures base pairing. The complementary strand synthesized from another primer, using the single-stranded nucleic acid as a template, is nuclease resistant. Accordingly, the restriction enzyme acts only at the restriction enzyme recognition site in the primer to thereby generate a nick. The complementary strand synthesis and displacement are repeatedly carried out, using this nick as the synthesis origin, to attain the amplification. At the same time, the primer for SDA also anneals to the single-stranded nucleic acid which is generated by the substitution, and the synthesis of the complementary strand is carried out.

The nucleic acid that serves as the template at this time is nuclease resistant, but, the nick produced by the restriction enzyme is generated in the primers for SDA since they are not nuclease resistant. As a result, the nucleic acid amplification reaction is also attained in the substituted single-stranded nucleic acid. Accordingly, by continuing the incubation in this condition, the double-stranded DNA, comprising the nucleotide sequences of the region which is prescribed by the primers for SDA, are successively synthesized, and, as a result, the amplification of the nucleic acid is attained. While the principle of the SDA method is already known, the present invention provides a novel finding, namely that the denaturing step of the double-stranded nucleic acid can be eliminated by initiating the reaction utilizing the nucleic acid synthesis reaction based on the destabilization of the double-strand.

In order to carry out the NASBA method based on the present invention, primers for the NASBA method are used in combination with the DNA polymerase and RNA polymerase which catalyze the strand displacement complementary strand synthesis reaction. The primers for the NASBA are constituted by the first primer to which the promoter sequence is added and the second primer which anneals to the complementary strand synthesized using the first primer as an origin.

First, the complementary strand synthesis is carried out using an arbitrary primer for the double-stranded template nucleic acid, and the region to which the first primer for NASBA should anneal is placed in a condition that ensures base pairing. Subsequently, the complementary strand synthesized using the first primer for NASBA as an origin is substituted by the outer primers to make it single-stranded. When the second primer for NASBA anneals to the obtained single-strand to make it double-stranded, the promoter region added to the first primer for NASBA becomes double-stranded. The transcription reaction using RNA polymerase is initiated by the promoter region, which has become double-stranded, and RNA synthesis is carried out using the target nucleotide sequence as a template.

Various reagents which are required for the nucleic acid synthesis method or the amplification method according to the present invention can be supplied as a kit which is previously packaged. Specifically, a kit of the present invention comprises oligonucleotides which are necessary as the inner primers and the outer primers, dNTP (which is the substrate of the complementary strand synthesis), DNA polymerase which carries out the strand displacement complementary strand synthesis, a buffer which provides a preferable condition for the enzyme reaction, further, if necessary, reagents required for detection of the product of the synthesis reaction, and the like. In particular, in the preferred embodiment of the present invention, since the addition of reagents is unnecessary during the reaction, the reagents necessary for one reaction can be supplied in a state that they are put in a reaction vessel so that the reaction can be initiated by only adding a sample. If a system in which the detection of the reaction product can be carried out in the reaction vessel using a light emitting signal or a fluorescent signal, is constructed, opening and closing of the vessel after the reaction can be abolished. This is very desirable from the viewpoint of preventing contamination.

All publications describing prior arts cited herein are incorporated herein by reference.

BEST MODE FOR CARRYING OUT THE INVENTION

Figure 1:
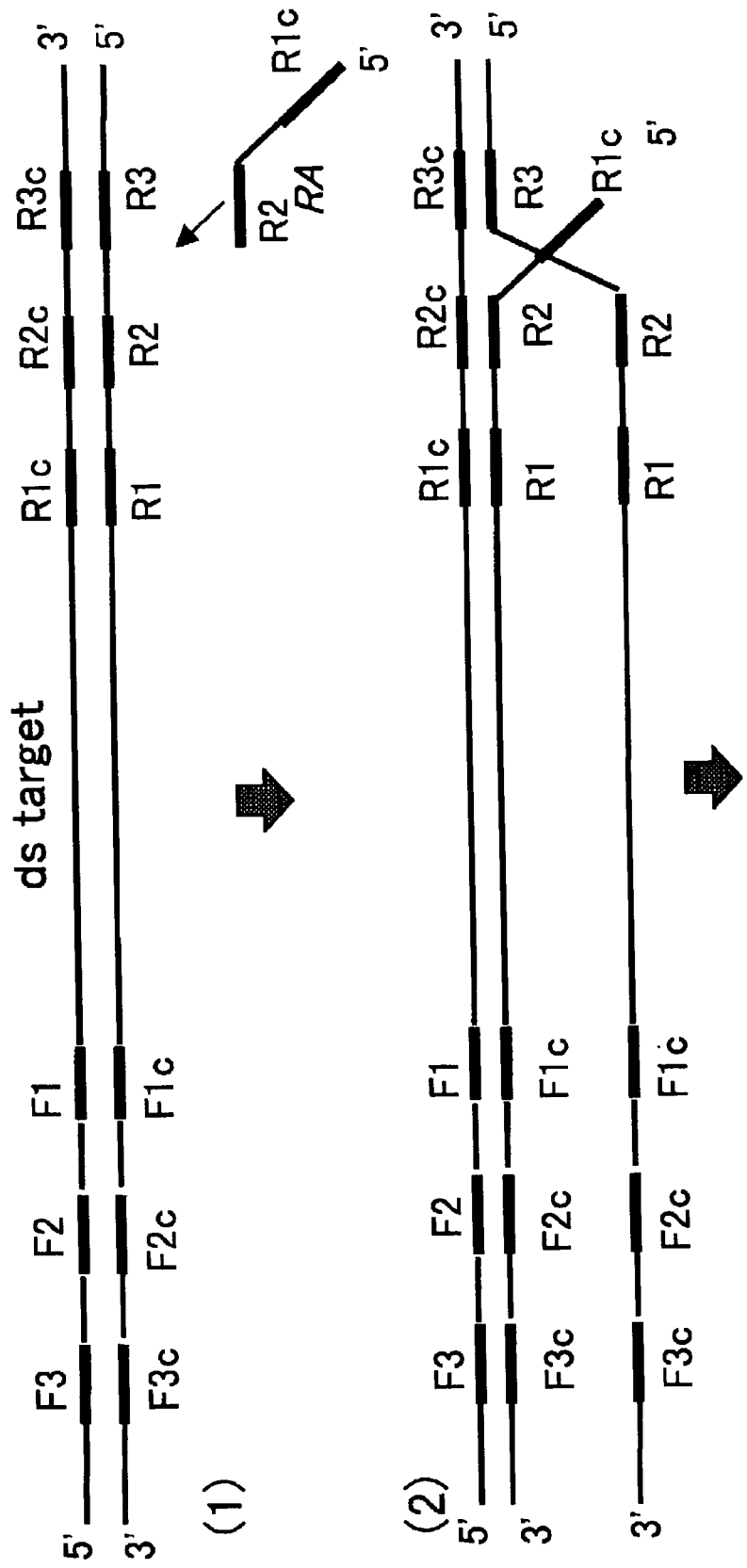
FIG. 1 schematically depicts parts (1) and (2) of the reaction principle of a preferred embodiment according to the present invention.
Figure 2:
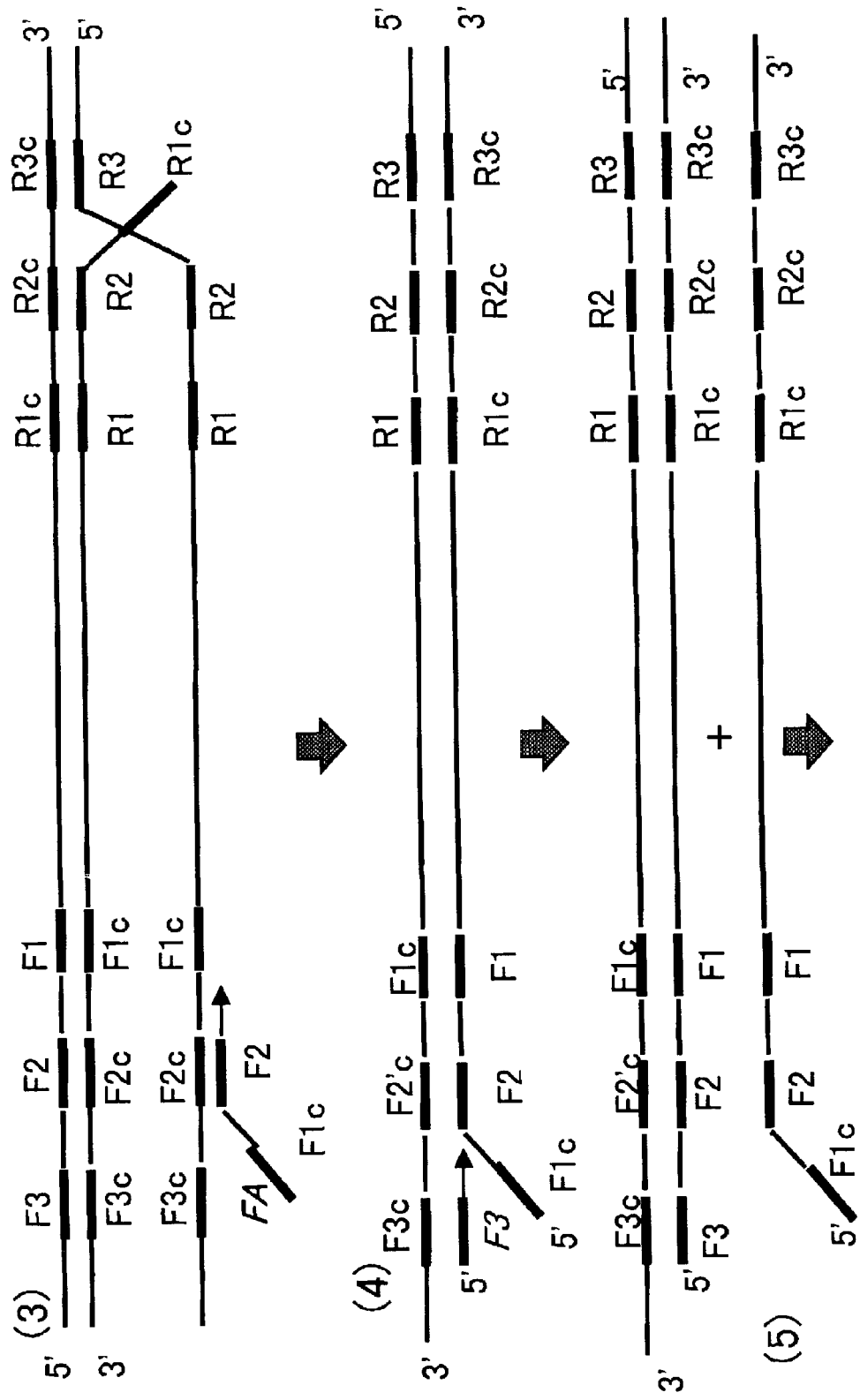
FIG. 2 schematically depicts parts (3) to (5) of the reaction principle of a preferred embodiment according to the present invention.
Figure 3:
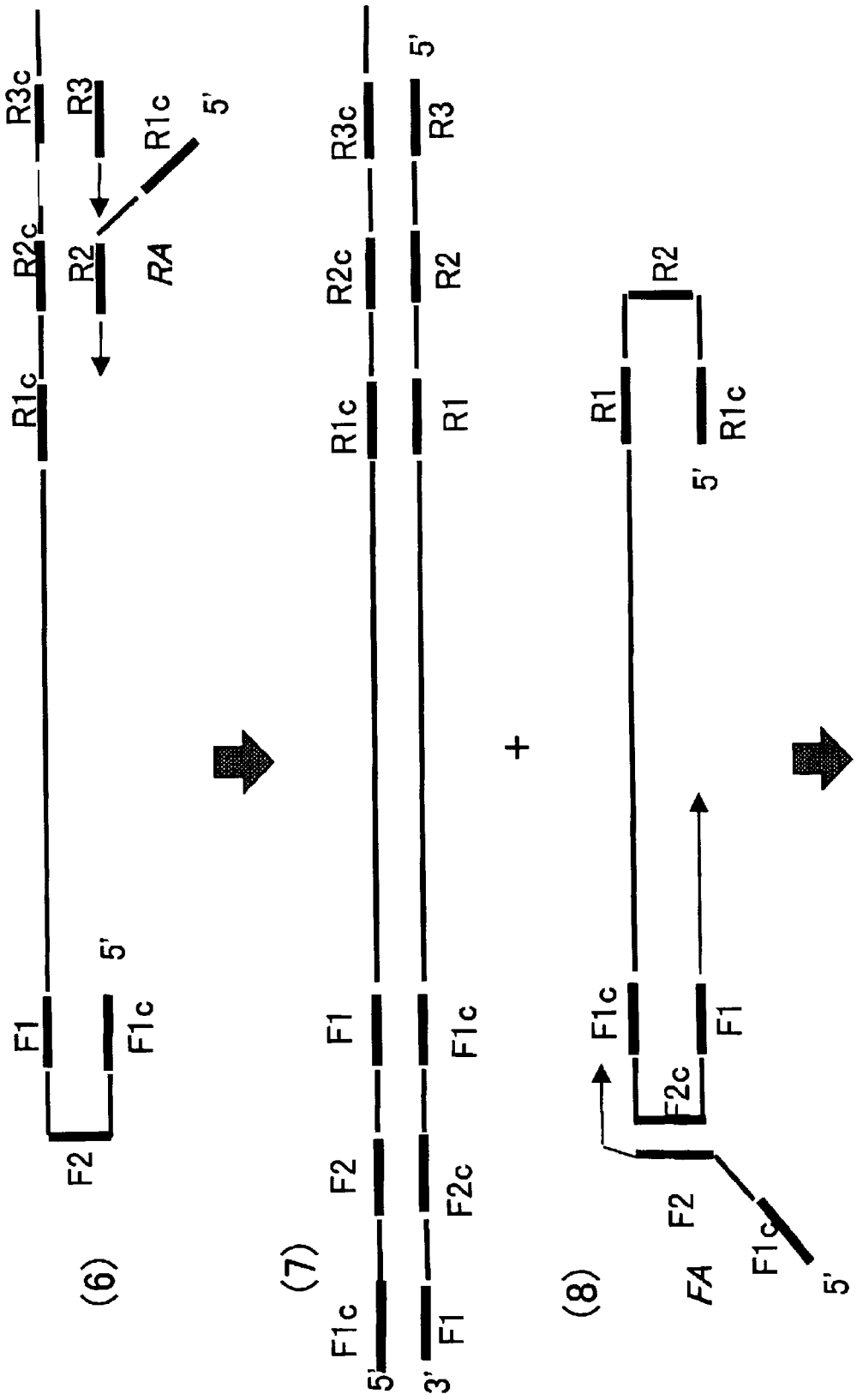
FIG. 3 schematically depicts parts (6) to (8) of the reaction principle of a preferred embodiment according to the present invention.
Figure 4:
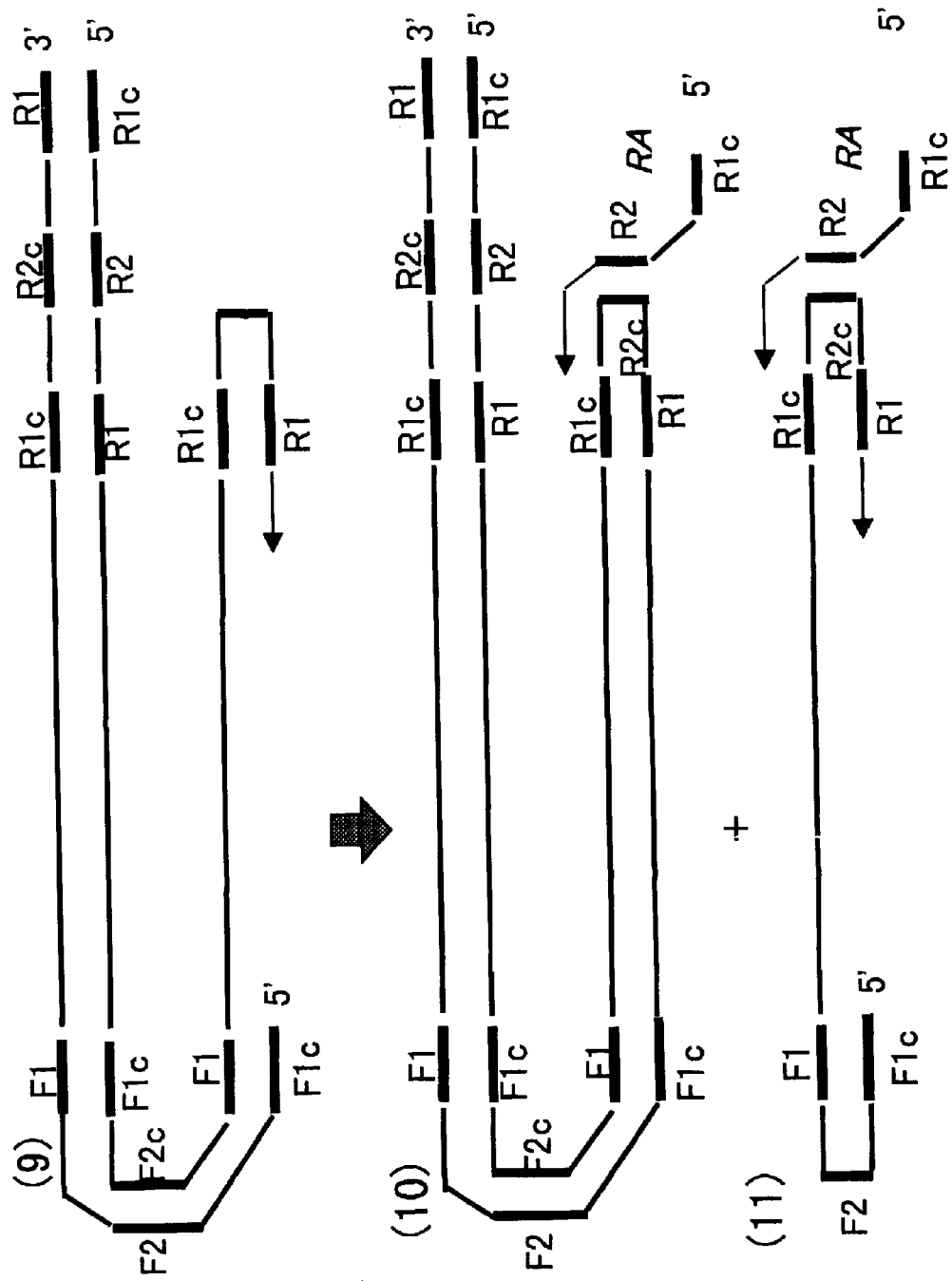
FIG. 4 schematically depicts parts (9) to (11) of the reaction principle of a preferred embodiment according to the present invention.

The present invention is further specifically illustrated below by way of Examples.

Example 1

Amplification of HBV, HCV, and PSA Gene Sequences

The nucleic acid synthesis method of the present invention was carried out using as a template a DNA (double-stranded) which was prepared by incorporating each of HBV, HCV, and PSA gene partial sequences in a plasmid. Four kinds of primers—Inner F, Inner R, Outer F, and Outer R—were used in the experiment. Outer F and the Outer R are outer primers for displacement of a first nucleic acid obtained using Inner F and Inner R, respectively, as synthesis origins.

The concentration of Inner F (or Inner R) was set high so that the annealing of the primer would predominantly occur. The template sequences of the present Example derived from HBV, HCV, and PSA which were incorporated in plasmids are shown in SEQ ID NO: 1, SEQ ID NO: 2, and SEQ ID NO: 3, respectively. Further, the sequences of the primers (Inner F, Inner R, Outer F, and Outer R) used for amplifying the respective templates are shown below.

HBV:

Inner F: (SEQ ID NO: 4):

5'-GATAAAACGCCGCAGACACATCCTTCCAACCTCTTGTCCTCCAA-3'

Inner R: (SEQ ID NO: 5)

5'-CCTGCTGCTATGCCTCATCTTCTTTGACAAACGGGCAACATACCTT-3'

Outer F: (SEQ ID NO: 6)

5'-CAAAATTCGCAGTCCCCAAC-3'

Outer R: (SEQ ID NO: 7)

5'-GGTGGTTGATGTTCCTGGA-3'

HCV:

Inner F: (SEQ ID NO: 8)

5'-GAGTGGGTTTATCCAAGAAAGGACTTTAGCCATAGTGGTCTGCGGA-3'

Inner R: (SEQ ID NO: 9)

5'-CTAGCCGAGTAGCGTTGGGTTGCTTTGCACTCGCAAGCACCCTATC-3'

Outer F: (SEQ ID NO: 10)

5'-GCAGAAAGCGTCTAGCCATGG-3'

Outer R: (SEQ ID NO: 11)

5'-CTAGCCGAGTAGCGTTGGGTTGC-3'

PSA:

Inner F: (SEQ ID NO: 12)

5'-TGTTCCTGATGCAGTGGGCAGCTTTAGTCTGCGGCGGTGTTCTG-3'

Inner K: (SEQ ID NO: 13)

5'-TGCTGGGTCGGCACAGCCTGAAGCTGACCTGAAATACCTGGCCTG-3'

Outer F: (SEQ ID NO: 14)

5'-TGCTTGTGGCCTCTCGTG-3'

Outer R: (SEQ ID NO: 15)

5'-GGGTGTGTGAAGCTGTG-3'

Further, the characteristics of the primer configuration are summarized below.

| Inner F: | |
|---|---|
| Primer | 5'-side region/3'-side region |
| Inner F | the same as the region F1c of the complementary strand synthesized using Inner F/ complementary to the region F2c of the template DNA |
| Inner R | the same as the region R1c of the complementary strand synthesized using Inner R/ complementary to the region R2c of the complementary strand synthesized using Inner F |
| Outer F | complementary to F3c adjacent to the 3'-side of the region F2c of the template DNA |
| Outer R | complementary to R3c adjacent to the 3'-side of the region R2c of the complementary strand synthesized using Inner F |

These primers synthesized the nucleic acid in which the region from the region F1c to R1c where the partial sequence of the individual gene was incorporated and its complementary nucleotide sequence are plurally connected on a single-strand sandwiching the loop-forming sequence containing F2c. The composition of the reaction solution for the nucleic acid synthesis method using these primers according to the present invention is shown below.

| Composition of reaction solution (in 25 µl) | |
|---|---|
| 20 mM | Tris-HCl, pH 8.8 |
| 10 mM | KCl |
| 10 mM | $(NH_4)_2SO_4$ |
| 4 mM | $MgSO_4$ |
| 1 M | Betaine |
| 0.1% | Triton X-100 |
| 0.4 mM | dNTP |
| 8 U | Bst DNA polymerase (NEW ENGLAND BioLabs) |
| Primer: | |
| 1600 nM | Inner F |
| 1600 nM | Inner R |
| 400 nM | Outer F |
| 400 nM | Outer R |
| Template: | |
| $1 \times 10^{-20}$ mol | HBV DNA |
| $1 \times 10^{-17}$ mol | HCV DNA |
| $1 \times 10^{-22}$ mol | PSA DNA |

As the template, those which are not thermally denatured were prepared. The reaction solution was reacted at 65° C. for one hour.

Figure 5:
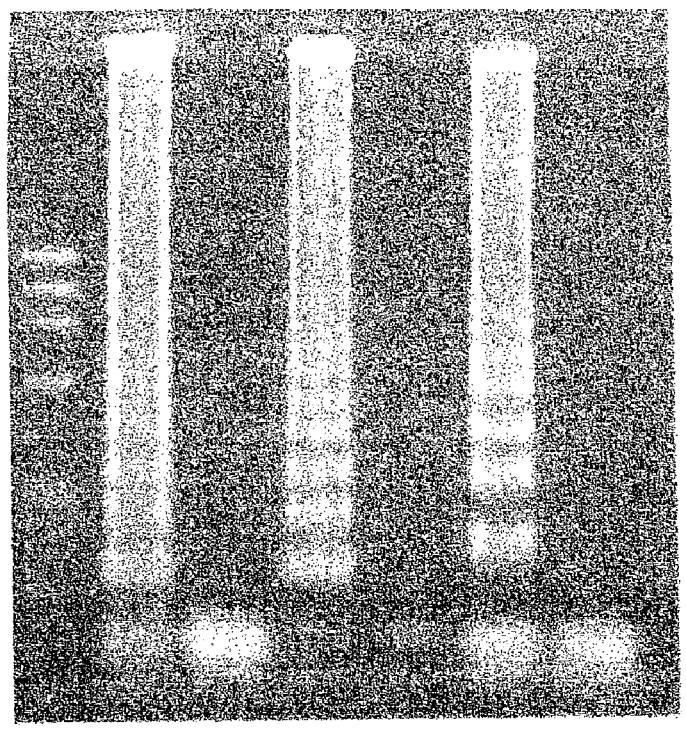
FIG. 5 is a photograph of an electrophoresis gel after an amplification reaction utilizing HBV, HCV, and PSA gene sequences.

Confirmation of reaction: 5 µL of loading buffer was added to 5 µL of the above reaction solution, and then, was loaded onto a 2% agarose gel (0.5% TBE). Electrophoresis was carried out for 0.5 hour at 100 V. As a molecular size marker, φ174 Hae III was used. After electrophoresis, the gel was stained with ethidium bromide (herein, abbreviated as EtBr) to visualize the nucleic acids. The result is depicted in FIG. 5. Each of the lanes corresponds to the following samples.

| Lane 1: | φX174 Hae III |
|---|---|
| Lane 2: | DNA (+), PSA |
| Lane 3: | DNA (−), PSA |
| Lane 4: | DNA (+), HBV |
| Lane 5: | DNA (−), HBV |
| Lane 6: | DNA (+), HCV |
| Lane 7: | DNA (−), HCV |

As the result of experiments, even in the cases of using any of DNAs such as HBV, HCV, and PSA as template, a ladder which is characteristic to the amplification product by the inner primers of the present invention was observed. It was confirmed that the synthesis of the nucleic acid is possible under a constant temperature condition using the double-stranded nucleic acid as a template and inner primers in combination with outer primers.

Example 2

Amplification in the Presence of Betaine

The nucleic acid synthesis method of the present invention was carried out using a DNA ($1 \times 10^{-17}$ moL) in which the partial sequence of HCV gene was incorporated in a plasmid, as a template. Four kinds of the primers—Inner F, Inner R, Outer F, and Outer R—were used in the experiment. At this time, a reaction solution which contained no betaine was also prepared.

As the template, those which are not thermally denatured were prepared. The reaction solutions were reacted at 65° C. for one hour and two hours.

Figure 6:
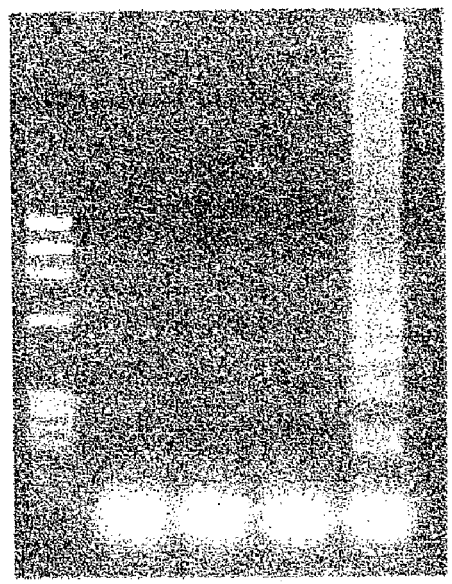
FIG. 6 is a photograph of an electrophoresis gel after the amplification reaction in the presence or absence of betaine.
Figure 6:
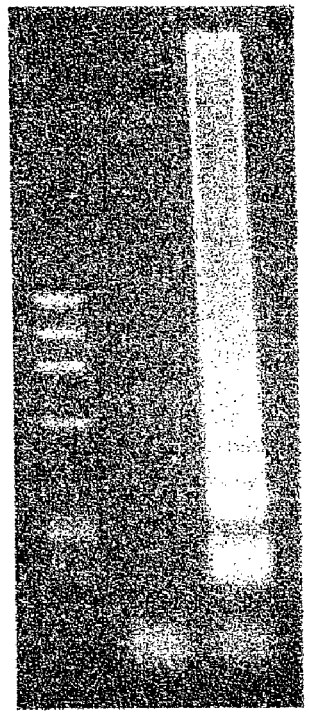

Confirmation of reaction: 5 μL of loading buffer was added to 5 μL of the above reaction solution, and then, was loaded onto a 2% agarose gel (0.5% TBE). Electrophoresis was carried out for 0.5 hour at 100 V. As a molecular size marker, φ174 Hae III was used. After electrophoresis, the gel was stained with EtBr to visualize the nucleic acids. The result is depicted in FIG. 6. Each of the lanes corresponds to the following samples.

| | |
|---|---|
| Lane 1: | φX174 Hae III |
| Lane 2: | DNA (−), Betaine (−), 1 h |
| Lane 3: | DNA (+), Betaine (−), 1 h |
| Lane 4: | DNA (−), Betaine (+), 1 h |
| Lane 5: | DNA (+), Betaine (+), 1 h |
| Lane 6: | φX174 Hae III |
| Lane 7: | DNA (−), Betaine (−), 2 h |
| Lane 8: | DNA (+), Betaine (−), 2 h |

As the result of experiments, when the reaction time was one hour, amplification was only observed in the presence of betaine. On the other hand, when the reaction time was extended to 2 hours, amplification was observed even in the absence of betaine. Namely, it could be confirmed that amplification is also observed in a usual reaction system.

Example 3

Amplification in Presence of Proline or DMSO

The nucleic acid synthesis method of the present invention was carried out using a DNA ($1\times10^{-17}$ mol) in which the partial sequence of HCV gene was incorporated in a plasmid, as a template. Four kinds of the primers—Inner F, Inner R, Outer F, and Outer R—were used in the experiments.

Proline or DMSO was added to the reaction solution in place of betaine so that the final concentration of proline or DMSO was 1% or 5%. The other composition of reaction solution was the same as that described above.

As the template, those which are not thermally denatured were prepared. The reaction solution was reacted at 65° C. for two hours.

Figure 7:
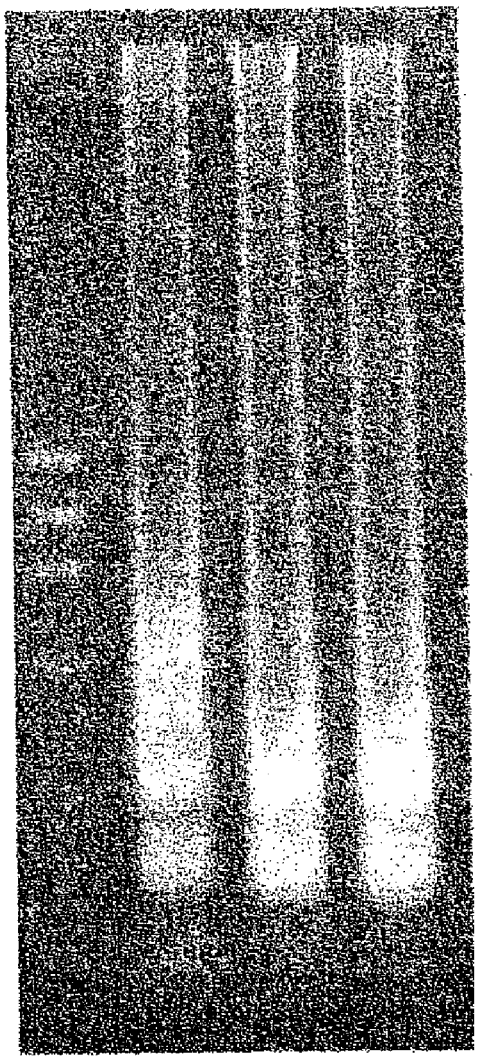
FIG. 7 is a photograph of an electrophoresis gel after the amplification reaction in the presence of proline and DMSO.

Confirmation of reaction: 5 μL of loading buffer was added to 5 μL of the above reaction solution, and then, was loaded onto a 2% agarose gel (0.5% TBE). Electrophoresis was carried out for 0.5 hour at 100 V. As a molecular size marker, φ174 Hae III was used. After electrophoresis, the gel was stained with EtBr to visualize the nucleic acids. The result is depicted in FIG. 7. Each of the lanes corresponds to the following samples.

| | |
|---|---|
| Lane 1: | φX174 Hae III |
| Lane 2: | proline (+) |
| Lane 3: | DMSO (+) |
| Lane 4: | Betaine (−) |

As the result of the amplification reaction using proline or DMSO which has a similar effect (the action for lowering a melting temperature) to betaine, it could be confirmed that the amplification reaction proceeded even if proline or DMSO was used.

Example 4

Influence of Outer Primers

The nucleic acid synthesis method according to the present invention was carried out using lambda DNA (SEQ ID NO: 16, $1\times10^5$ molecule) which is a linear strand and serves as the target nucleotide sequence. Four kinds of primers—Inner F, Inner R. Outer F, and Outer R—were used for the experiment. Reactions in which primers Outer F and Outer R were not used were carried out at the same time. Ethidium bromide (EtBr) was added to all of the reaction systems to a final concentration of 0.25 μg/ml.

The target, which is not thermally denatured, was prepared. The reaction solutions were reacted at 65° C. for 1.5 hours, and the change in fluorescence intensity was observed in the lapse of time using ABI 7700 (Perkin Elmer). EtBr is a fluorescent staining agent which is specific to the double-stranded nucleic acid. Accordingly, the fluorescence intensity is increased depending on the amount of the double-stranded nucleic acid which is generated by the nucleic acid amplification.

Figure 8:
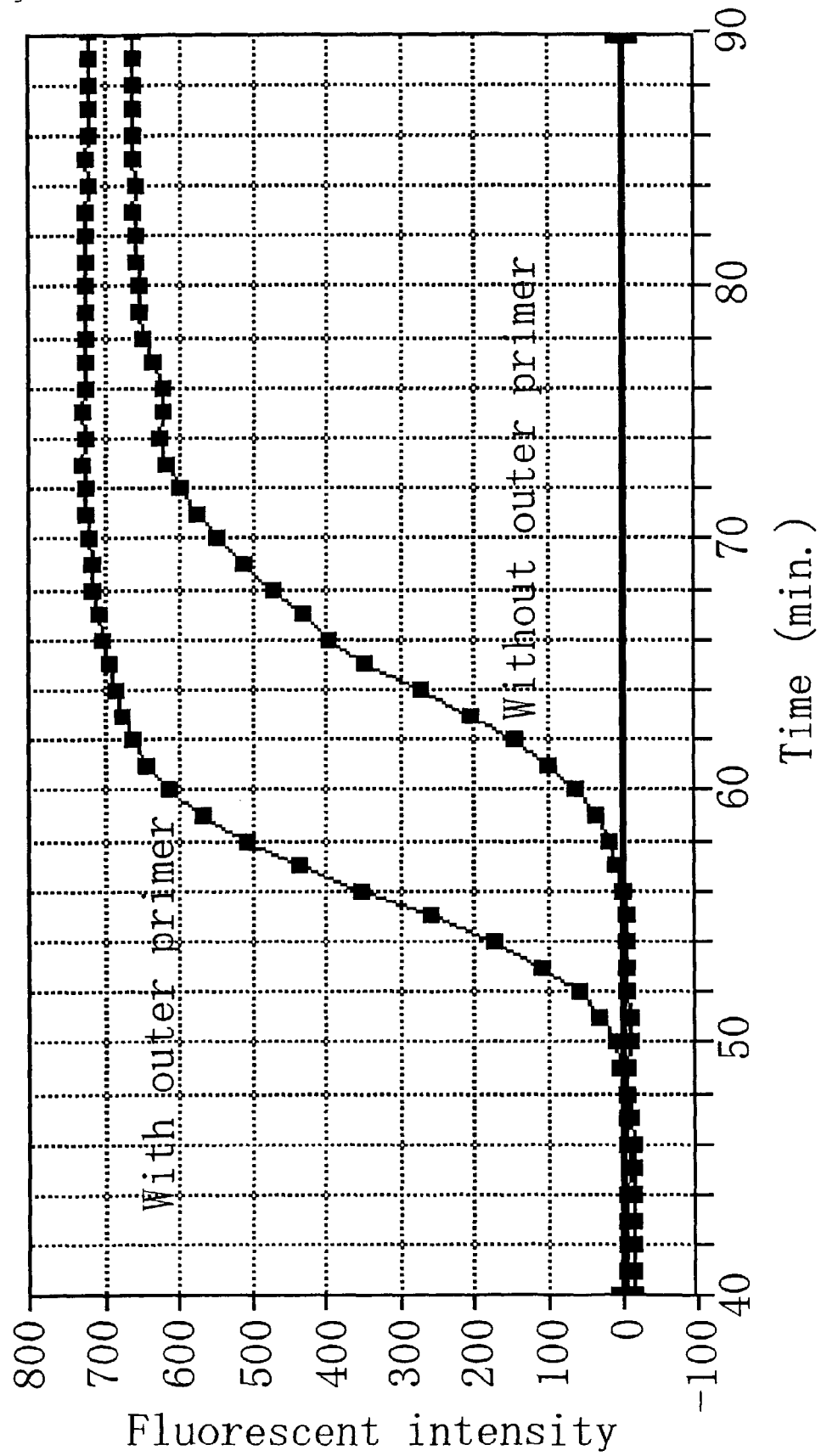
FIG. 8 is a graph showing a result of observing the influence of an outer primer on the nucleic acid amplification method of the present invention. The vertical axis and horizontal axis indicate fluorescent intensity and reaction time, respectively.

The measurement result is shown in FIG. 8. It was found that the amplification rate was slow in the reaction system without the outer primers.

```
The nucleotide sequence of lambda DNA primer
Inner F:                                      (SEQ ID NO: 17)
CAGCCAGCCGCAGCACGTTCGCTCATAGGAGATATGGTAGAGCCGC Inner R:                                      (SEQ ID NO: 18)
GAGAGAATTTGTACCACCTCCCACCGGGCACATAGCAGTCCTAGGGACAGT Outer F:                                      (SEQ ID NO: 19)
GGCTTGGCTCTGCTAACACGTT Outer R:                                      (SEQ ID NO: 20)
GGACGTTTGTAATGTCCGCTCC
```

INDUSTRIAL APPLICABILITY

The present invention provides a nucleic acid synthesis method that eliminates the need for temperature change without deteriorating the specificity and efficiency of the reaction. Although the present invention uses double-stranded nucleic acid as a template, the temperature change for denaturing is unnecessary. Accordingly, the synthesis of the nucleic acid can be carried out without using equipment having a specific temperature control mechanism. Further, according to the present invention which does not require thermal cycling, a non-specific reaction caused by the temperature change can be expectedly prevented.

The nucleic acid synthesis method according to the present invention can be applied to any nucleic acid synthesis methods based on a principle using a primer as a synthesis origin. In particular, higher synthesis efficiency can be attained when combined with the nucleic acid synthesis reaction based on a principle which does not originally require a temperature change. The nucleic acid amplification method, for example, as shown in Examples, which provides an amplified product with a configuration in which the 3'-terminal region can anneal to a portion of itself, can achieve excellent operability and specificity when combined with the present invention. A high level of amplification efficiency can be attained by only incubating the double-stranded nucleic acid, which becomes a template, together with a primer and DNA polymerase at a constant temperature. The present invention enables a nucleic acid amplification method which does not require a temperature change while keeping high specificity and high amplification efficiency.

Since the nucleic acid synthesis method based on the present invention does not require temperature changes, the monitoring of the reaction can be easily carried out. Namely, an incubation mechanism providing a constant temperature and equipment with an optical reading mechanism can be used to monitor the reaction. Such mechanism is a general mechanism provided in conventional optical analysis equipment. Accordingly, the nucleic acid amplification method based on the present invention enables monitoring by conventional analysis equipment.

As described above, the nucleic acid synthesis method according to the present invention does not require a complicated temperature control, which is a problem associated with known methods, such as the PCR methods, and remarkably simplifies the experimental operation. Further, the present invention enables a nucleic acid amplification method which does not require specific equipment for temperature control and is thus generally usable. Further, in the present invention, the non-specific reaction caused by the temperature change can be prevented.

The invention claimed is:

1. A method for amplifying a double-stranded nucleic acid template comprising a specific region, wherein the method comprises:

a) initiating incubation of the double-stranded nucleic acid template and an arbitrary primer in the presence of a DNA polymerase that catalyzes a complementary strand synthesis reaction accompanying strand displacement under a condition that ensures the synthesis of the complementary strand using the arbitrary primer as an origin without denaturation of the double-stranded nucleic acid template, such that a region on one strand of the double-stranded nucleic acid template located 3' of the specific region and to be annealed by a second primer, is placed in a condition that allows the region to undergo base pairing;

b) annealing the second primer to the region obtained in step a) and carrying out complementary strand synthesis using the second primer as an origin to obtain an extended product, wherein the 3'-end of the second primer anneals to the region obtained in step a) and the 5'-end of the second primer comprises a nucleotide sequence complementary to an arbitrary region of the extended product obtained using the second primer as an origin;

c) placing a region of the extended product of the second primer synthesized in step b), located 3' of the specific region and to be annealed by a first primer, in a condition such that the region can undergo base pairing, wherein the 3∝-end of the first primer anneals to the region of the extended product obtained using the second primer as an origin, and step c) is carried out by displacement according to a complementary strand synthesis reaction using as an origin a fourth primer that anneals to the 3'-side of the region of the template annealed by the 3' end of the second primer;

d) annealing the first primer to the region obtained in step c) and carrying out complementary strand synthesis using the first primer as an origin to obtain an extended product of the first primer;

e) allowing self annealing at the 3'-end of the extended product of the first primer synthesized in step d) to occur, thereby forming a loop, and carrying out complementary strand synthesis using the extended product of step d) as a template and the 3' end of the formed loop as an origin to obtain a nucleic acid in which a plurality of copies of the specific region are connected on a single strand, wherein the step further comprises a step of converting the extended product of the first primer into a single strand by displacement according to a complementary strand synthesis reaction using as an origin a third primer that anneals to the 3'-side of the region of the template annealed by the 3' end of the first primer, wherein (i) the displacement in step c) is carried out beginning from where the 3' end portion of the fourth primer anneals to the region obtained in step a) and continues to at least the portion of the extended product of the second primer to which the first primer anneals, (ii) the displacement in step e) is carried out beginning from where the 3' end portion of the third primer anneals to the region obtained in step c) and continues to the 3' end of the extended product of the first primer, or (iii) both (i) and (ii) are carried out; and further comprising:

f) allowing self annealing at the 3'-end of the nucleic acid produced by the complementary strand synthesis in step e) to form a loop and carrying out complementary strand synthesis using the 3' end of the formed loop as an origin and the nucleic acid as a template;

g) annealing the second primer to the loop that is formed in step e) and the first primer to the loop that is formed in step f), and carrying out complementary strand synthesis using the first and second primers as an origin;

h) allowing strand displacement of the extended product of step f) so that the 3'-end thereof can undergo base pairing to form a loop;

i) carrying out complementary strand synthesis using as a template the displaced strand obtained in step h), and using the loop formed at its 3'-end as an origin to displace a complementary strand synthesized in step g), thereby producing a single-stranded nucleic acid comprising a plurality of copies of the specific region connected on the single strand; and j) repeating steps g) to i) to amplify the nucleic acid in which the plurality of copies of the specific region are connected on the single strand.

2. The method according to claim 1, wherein the method further comprises:

k) allowing self annealing of the 3'-end of the single-stranded nucleic acid produced in step i) to form a loop;

l) annealing the first primer to the loop that is formed in step k) and carrying out complementary strand synthesis using the first primer as an origin;

m) allowing strand displacement of the extended product of step l), so that the 3'-end can undergo base pairing to form a loop;

n) carrying out complementary strand synthesis using as a template the displaced strand obtained in step m) and using the loop at its 3'-end as an origin to displace a complementary strand synthesized in the step l), thereby producing a single-stranded nucleic acid; and o) repeating steps l) to n) to amplify the nucleic acid in which a plurality of copies of the specific region are connected on a single strand.

3. A method for detecting a target nucleotide sequence in a sample, the method comprising carrying out the amplification method according to claim 1 and observing whether or not the amplification reaction product has been generated.

4. The method according to claim 3, wherein the method is carried out in the presence of a nucleic acid detection agent, the method further comprising determining whether or not the amplification reaction product has been generated based on the signal change of the detection agent.

5. A method for detecting mutation of a target nucleotide sequence by amplification, said method comprising:

a) initiating incubation of a double-stranded nucleic acid template comprising a specific region and an arbitrary primer in the presence of a DNA polymerase that catalyzes a complementary strand synthesis reaction accompanying strand displacement under a condition that ensures the synthesis of the complementary strand using the arbitrary primer as an origin without denaturation of the double-stranded nucleic acid template, such that a region on one strand of the double-stranded nucleic acid template located 3' of the specific region and to be annealed by a second primer, is placed in a condition that allows the region to undergo base pairing;

b) annealing the second primer to the region obtained in step a) and carrying out complementary strand synthesis using the second primer as an origin to obtain an extended product, wherein the 3'-end of the second primer anneals to the region obtained in step a) and the 5'-end of the second primer comprises a nucleotide sequence complementary to an arbitrary region of the extended product obtained using the second primer as an origin;

c) placing a region of the extended product of the second primer synthesized in step b), located 3∝ of the specific region and to be annealed by a first primer, in a condition such that the region can undergo base pairing, wherein the 3'-end of the first primer anneals to the region of the extended product obtained using the second primer as an origin, and step c) is carried out by displacement according to a complementary strand synthesis reaction using as an origin a fourth primer that anneals to the 3'-side of the region of the template annealed by the 3' end of the second primer;

d) annealing the first primer to the region obtained in step c) and carrying out complementary strand synthesis using the first primer as an origin to obtain an extended product of the first primer;

e) allowing self annealing at the 3'-end of the extended product of the first primer synthesized in step d) to occur, thereby forming a loop, and carrying out complementary strand synthesis using the extended product of step d) as a template and the 3' end of the formed loop as an origin to obtain a nucleic acid in which a plurality of copies of the specific region are connected on a single strand, wherein the step further comprises a step of converting the extended product of the first primer into a single strand by displacement according to a complementary strand synthesis reaction using as an origin a third primer that anneals to the 3'-side of the region of the template annealed by the 3' end of the first primer, wherein (i) the displacement in step c) is carried out beginning from where the 3' end portion of the fourth primer anneals to the region obtained in step a) and continues to at least the portion of the extended product of the second primer to which the first primer anneals, (ii) the displacement in step e) is carried out beginning from where the 3' end portion of the third primer anneals to the region obtained in step c) and continues to the 3' end of the extended product of the first primer, or (iii) both (i) and (ii) are carried out; and further comprising:

f) allowing self annealing at the 3'-end of the nucleic acid produced by the complementary strand synthesis in step e) to form a loop and carrying out complementary strand synthesis using the 3' end of the formed loop as an origin and the nucleic acid as a template;

g) annealing the second primer to the loop that is formed in step e) and the first primer to the loop that is formed in step f), and carrying out complementary strand synthesis using the first and second primer as an origin;

h) allowing strand displacement of the extended product of step f) so that the 3'-end can undergo base pairing to form a loop;

i) carrying out complementary strand synthesis using as a template the displaced strand obtained in step h) and using the loop at its 3'-end as an origin to displace a complementary strand synthesized in step g), thereby producing a single-stranded nucleic acid;

j) repeating steps g) to i) to amplify the nucleic acid in which a plurality of copies of the specific region are connected on a single strand;

k) allowing self annealing of the 3'-end of the single-stranded nucleic acid produced in step i) to form a loop;

l) annealing the first primer to the loop that is formed in step k) and carrying out complementary strand synthesis using the first primer as an origin;

m) allowing strand displacement of the extended product of step l), so that the 3'-end can undergo base pairing to form a loop;

n) carrying out complementary strand synthesis using as a template the displaced strand obtained in step m) and using the loop at its 3'-end as an origin to displace a complementary strand synthesized in step l) using the loop region as an origin, thereby producing a single-stranded nucleic acid;

o) repeating steps l) to n) to conduct an amplification reaction; and p) observing whether or not an amplification reaction product has been generated;

wherein mutation in a nucleotide sequence to be amplified prevents the synthesis of the complementary strand at least at one 3'-end that is an origin of complementary strand synthesis.

* * * * *

UNITED STATES PATENT AND TRADEMARK OFFICE
CERTIFICATE OF CORRECTION

PATENT NO. : 8,017,357 B2  
APPLICATION NO. : 10/240460  
DATED : September 13, 2011  
INVENTOR(S) : Notomi et al.

It is certified that error appears in the above-identified patent and that said Letters Patent is hereby corrected as shown below:

In Claim 1, at Col. 38, line 61, delete "3∝" and insert --3'--.

In Claim 5, at Col. 40, line 39, delete "3∝" and insert --3'--.

Signed and Sealed this  
Twenty-ninth Day of November, 2011

David J. Kappos  
*Director of the United States Patent and Trademark Office*

```
                              SEQUENCE LISTING

<160> NUMBER OF SEQ ID NOS: 20

<210> SEQ ID NO 1
<211> LENGTH: 198
<212> TYPE: DNA
<213> ORGANISM: Hepatitis B virus

<400> SEQUENCE: 1
caaaattcgc agtccccaac ctccaatcac tcaccaacct cttgtcctcc aatttgtcct      60
ggctatcgct ggatgtgtct gcggcgtttt atcatattcc tcttcatcct gctgctatgc     120
ctcatcttct tgttggttct tctggactac caaggtatgt tgcccgtttg tcctctactt     180
ccaggaacat caaccacc                                                   198

<210> SEQ ID NO 2
<211> LENGTH: 279
<212> TYPE: DNA
<213> ORGANISM: Hepatitis C virus

<400> SEQUENCE: 2
gcagaaagcg tctagccatg gcgttagtat gagtgtcgta cagcctccag gcccccccct      60
cccgggagag ccatagtggt ctgcggaacc ggtgagtaca ccggaattac cggaaagact     120
gggtcctttc ttggataaac ccactctatg tccggtcatt tgggcgtgcc cccgcaagac     180
tgctagccga gtagcgttgg gttgcgaaag gccttgtggt actgcctgat agggtgcttg     240
cgagtgcccc gggaggtctc gtagaccgtg catcatgag                            279

<210> SEQ ID NO 3
<211> LENGTH: 178
<212> TYPE: DNA
<213> ORGANISM: Homo sapiens

<400> SEQUENCE: 3
tgcttgtggc ctctcgtggc agggcagtct gcggcggtgt tctggtgcac ccccagtggg      60
tcctcacagc tgcccactgc atcaggaaca aaagcgtgat cttgctgggt cggcacagcc     120
tgtttcatcc tgaagacaca ggccaggtat ttcaggtcag ccacagcttc acacaccc      178

<210> SEQ ID NO 4
<211> LENGTH: 44
<212> TYPE: DNA
<213> ORGANISM: Artificial Sequence
<220> FEATURE:
<223> OTHER INFORMATION: Description of Artificial Sequence:
      Artificially synthesized primer sequence
```

-continued

<400> SEQUENCE: 4
gataaaacgc cgcagacaca tccttccaac ctcttgtcct ccaa            44

<210> SEQ ID NO 5
<211> LENGTH: 46
<212> TYPE: DNA
<213> ORGANISM: Artificial Sequence
<220> FEATURE:
<223> OTHER INFORMATION: Description of Artificial Sequence:
      Artificially synthesized primer sequence

<400> SEQUENCE: 5
cctgctgcta tgcctcatct tctttgacaa acgggcaaca tacctt          46

<210> SEQ ID NO 6
<211> LENGTH: 20
<212> TYPE: DNA
<213> ORGANISM: Artificial Sequence
<220> FEATURE:
<223> OTHER INFORMATION: Description of Artificial Sequence:
      Artificially synthesized primer sequence

<400> SEQUENCE: 6
caaaattcgc agtccccaac                                        20

<210> SEQ ID NO 7
<211> LENGTH: 19
<212> TYPE: DNA
<213> ORGANISM: Artificial Sequence
<220> FEATURE:
<223> OTHER INFORMATION: Description of Artificial Sequence:
      Artificially synthesized primer sequence

<400> SEQUENCE: 7
ggtggttgat gttcctgga                                         19

<210> SEQ ID NO 8
<211> LENGTH: 46
<212> TYPE: DNA
<213> ORGANISM: Artificial Sequence
<220> FEATURE:
<223> OTHER INFORMATION: Description of Artificial Sequence:
      Artificially synthesized primer sequence

<400> SEQUENCE: 8
gagtgggttt atccaagaaa ggactttagc catagtggtc tgcgga           46

<210> SEQ ID NO 9
<211> LENGTH: 46
<212> TYPE: DNA
<213> ORGANISM: Artificial Sequence
<220> FEATURE:
<223> OTHER INFORMATION: Description of Artificial Sequence:
      Artificially synthesized primer sequence

<400> SEQUENCE: 9
ctagccgagt agcgttgggt tgctttgcac tcgcaagcac cctatc           46

<210> SEQ ID NO 10
<211> LENGTH: 21
<212> TYPE: DNA
<213> ORGANISM: Artificial Sequence
<220> FEATURE:
<223> OTHER INFORMATION: Description of Artificial Sequence:
      Artificially synthesized primer sequence

```
<400> SEQUENCE: 10
gcagaaagcg tctagccatg g                                              21

<210> SEQ ID NO 11
<211> LENGTH: 23
<212> TYPE: DNA
<213> ORGANISM: Artificial Sequence
<220> FEATURE:
<223> OTHER INFORMATION: Description of Artificial Sequence:
      Artificially synthesized primer sequence

<400> SEQUENCE: 11
ctagccgagt agcgttgggt tgc                                            23

<210> SEQ ID NO 12
<211> LENGTH: 44
<212> TYPE: DNA
<213> ORGANISM: Artificial Sequence
<220> FEATURE:
<223> OTHER INFORMATION: Description of Artificial Sequence:
      Artificially synthesized primer sequence

<400> SEQUENCE: 12
tgttcctgat gcagtgggca gctttagtct gcggcggtgt tctg                     44

<210> SEQ ID NO 13
<211> LENGTH: 45
<212> TYPE: DNA
<213> ORGANISM: Artificial Sequence
<220> FEATURE:
<223> OTHER INFORMATION: Description of Artificial Sequence:
      Artificially synthesized primer sequence

<400> SEQUENCE: 13
tgctgggtcg gcacagcctg aagctgacct gaaatacctg gcctg                    45

<210> SEQ ID NO 14
<211> LENGTH: 18
<212> TYPE: DNA
<213> ORGANISM: Artificial Sequence
<220> FEATURE:
<223> OTHER INFORMATION: Description of Artificial Sequence:
      Artificially synthesized primer sequence

<400> SEQUENCE: 14
tgcttgtggc ctctcgtg                                                  18

<210> SEQ ID NO 15
<211> LENGTH: 17
<212> TYPE: DNA
<213> ORGANISM: Artificial Sequence
<220> FEATURE:
<223> OTHER INFORMATION: Description of Artificial Sequence:
      Artificially synthesized primer sequence

<400> SEQUENCE: 15
gggtgtgtga agctgtg                                                   17

<210> SEQ ID NO 16
<211> LENGTH: 245
<212> TYPE: DNA
<213> ORGANISM: Bacteriophage lambda

<400> SEQUENCE: 16
ggcttggctc tgctaacacg ttgctcatag gagatatggt agagccgcag acacgtcgta    60
tgcaggaacg tgctgcggct ggctggtgaa cttccgatag tgcgggtgtt gaatgatttc   120
```

```
cagttgctac cgattttaca tatttttgc atgagagaat ttgtaccacc tcccaccgac      180
catctatgac tgtacgccac tgtccctagg actgctatgt gccggagcgg acattacaaa    240
cgtcc                                                                245

<210> SEQ ID NO 17
<211> LENGTH: 46
<212> TYPE: DNA
<213> ORGANISM: Artificial Sequence
<220> FEATURE:
<223> OTHER INFORMATION: Description of Artificial Sequence:
      Artificially synthesized primer sequence

<400> SEQUENCE: 17
cagccagccg cagcacgttc gctcatagga gatatggtag agccgc                   46

<210> SEQ ID NO 18
<211> LENGTH: 51
<212> TYPE: DNA
<213> ORGANISM: Artificial Sequence
<220> FEATURE:
<223> OTHER INFORMATION: Description of Artificial Sequence:
      Artificially synthesized primer sequence

<400> SEQUENCE: 18
gagagaattt gtaccacctc ccaccgggca catagcagtc ctagggacag t             51

<210> SEQ ID NO 19
<211> LENGTH: 22
<212> TYPE: DNA
<213> ORGANISM: Artificial Sequence
<220> FEATURE:
<223> OTHER INFORMATION: Description of Artificial Sequence:
      Artificially synthesized primer sequence

<400> SEQUENCE: 19
ggcttggctc tgctaacacg tt                                             22

<210> SEQ ID NO 20
<211> LENGTH: 22
<212> TYPE: DNA
<213> ORGANISM: Artificial Sequence
<220> FEATURE:
<223> OTHER INFORMATION: Description of Artificial Sequence:
      Artificially synthesized primer sequence

<400> SEQUENCE: 20
ggacgtttgt aatgtccgct cc                                             22
```